US010725018B2

(12) United States Patent
Nadkarni et al.

(10) Patent No.: US 10,725,018 B2
(45) Date of Patent: Jul. 28, 2020

(54) OPTICAL THROMBOELASTOGRAPHY SYSTEMS AND METHODS

(71) Applicant: THE GENERAL HOSPITAL CORPORATION, Boston, MA (US)

(72) Inventors: Seemantini K. Nadkarni, Cambridge, MA (US); Zeinab Hajjarian, Cambridge, MA (US); Markandey Tripathi, Auburndale, MA (US); Diane Tshikudi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 157 days.

(21) Appl. No.: 15/319,093

(22) PCT Filed: Jun. 1, 2015

(86) PCT No.: PCT/US2015/033464
§ 371 (c)(1),
(2) Date: Dec. 15, 2016

(87) PCT Pub. No.: WO2015/184433
PCT Pub. Date: Dec. 3, 2015

(65) Prior Publication Data
US 2017/0122930 A1    May 4, 2017

Related U.S. Application Data

(60) Provisional application No. 62/005,216, filed on May 30, 2014.

(51) Int. Cl.
*G01N 33/49*    (2006.01)
*G01N 33/86*    (2006.01)
(Continued)

(52) U.S. Cl.
CPC .... *G01N 33/4905* (2013.01); *B01L 3/502715* (2013.01); *G01N 11/00* (2013.01);
(Continued)

(58) Field of Classification Search
CPC .. G01N 33/4905; G01N 21/272; G01N 15/00; G01N 21/51; G01N 21/82; G01N 11/00; G01N 33/86; B01L 3/502715
See application file for complete search history.

(56) References Cited

U.S. PATENT DOCUMENTS 6,472,161 B1 * 10/2002 Baugh ................... G01N 33/86
                                                          435/13
2003/0064505 A1 * 4/2003 Harttig ............... G01N 33/4905
                                                          435/287.1
(Continued)

FOREIGN PATENT DOCUMENTS

| WO | 2007025559 A1 | 3/2007 |
| WO | 2014100378 A1 | 6/2014 |
| WO | 2015160418 A2 | 10/2015 |

OTHER PUBLICATIONS

Zhou, et al., Platelet Aggregation Testing in Platelet-Rich Plasma, Coagulation and Transfusion Medicine, 2005, 123: 172-183. (Year: 2005).*

(Continued)

*Primary Examiner* — Matthew D Krcha
(74) *Attorney, Agent, or Firm* — Quarles & Brady LLP

(57) ABSTRACT

Hand-held optical thromboelastographic sensor and method of using the same for simultaneous assessment of multiple parameters of blood coagulation at a point-of-care. The sensor includes an optical system registering laser speckle intensities associated with portions of a blood sample delivered through a fluid switch to analysis chambers of a cartridge of the sensor, and data-processing circuitry programmed to derive the multiple parameters from speckle (Continued)

intensity. The circuitry may be part of a mobile device configured to operate without communication with a central server and/or data storage.

26 Claims, 19 Drawing Sheets

(51) Int. Cl.
| | |
|---|---|
| *G01N 21/51* | (2006.01) |
| *G01N 21/82* | (2006.01) |
| *G01N 11/00* | (2006.01) |
| *G01N 15/00* | (2006.01) |
| *G01N 21/27* | (2006.01) |
| *B01L 3/00* | (2006.01) |
| *G01N 15/02* | (2006.01) |
| *G01N 21/47* | (2006.01) |

(52) U.S. Cl.
CPC ........... *G01N 15/00* (2013.01); *G01N 21/272* (2013.01); *G01N 21/51* (2013.01); *G01N 21/82* (2013.01); *G01N 33/86* (2013.01); *B01L 2300/0654* (2013.01); *B01L 2300/0816* (2013.01); *B01L 2300/0864* (2013.01); *B01L 2400/0487* (2013.01); *B01L 2400/0688* (2013.01); *G01N 2015/0092* (2013.01); *G01N 2015/0222* (2013.01); *G01N 2021/479* (2013.01); *G01N 2021/825* (2013.01); *G01N 2201/0221* (2013.01); *G01N 2203/0094* (2013.01)

(56) References Cited

U.S. PATENT DOCUMENTS

| | | | |
|---|---|---|---|
| 2004/0235147 A1* | 11/2004 | Chappell | B01L 3/508 435/287.2 |
| 2005/0233466 A1* | 10/2005 | Wright | G01N 11/14 436/165 |
| 2010/0248278 A1 | 9/2010 | Pouteau et al. | |
| 2012/0301967 A1* | 11/2012 | Nadkarni | A61B 5/14546 436/69 |

OTHER PUBLICATIONS

The International Search Report and Written Opinion dated Aug. 31, 2015 for International Application No. PCT/US2015/033464.
Faivre, et al., Coagulation Dynamics of a Blood Sample by Multiple Scattering Analysis, Journal of Biomedical Optics, 2011, 16(5):057001-1-057001-9.
Haas, et al., The In Vitro Effects of Fibrinogen Concentrate, Factor XIII and Fresh Frozen Plasma on Impaired Clot Formation After 60% Dilution, Anesth. Analg., 2008, 106(5):1360-1365.
Piederriere, et al., Particle Aggregation Monitoring by Speckle Size Measurement; Application to Blood Platelets Aggregation, Optics Express, 2004, 12(19):4596-4601.
Tripathi, et al., Assessing Blood Coagulation Status with Laser Speckle Rheology, Biomedical Optics Express, 2014, 5(3):817-831.
Viola, et al., A Novel Ultrasound-Based Method to Evaluate Hemostatic Function of Whole Blood, Clin. Chim. Acta, 2010, 411(1-2):106-113.
European Patent Office, Extended European Search Report, Application No. 15799372.6, dated Jan. 24, 2018.

* cited by examiner

OTEG configuration:
DL: diode laser (690nm)
M: mirror
P1, P2: polarizers
L1-L4: lenses
BS: beam splitter
S: sample cartridge
HT: heated stage
IMAQ: image acquisition card
MC: microprocessor/computer
TC: temperature controller electronics
LCD: display FIG. 9A
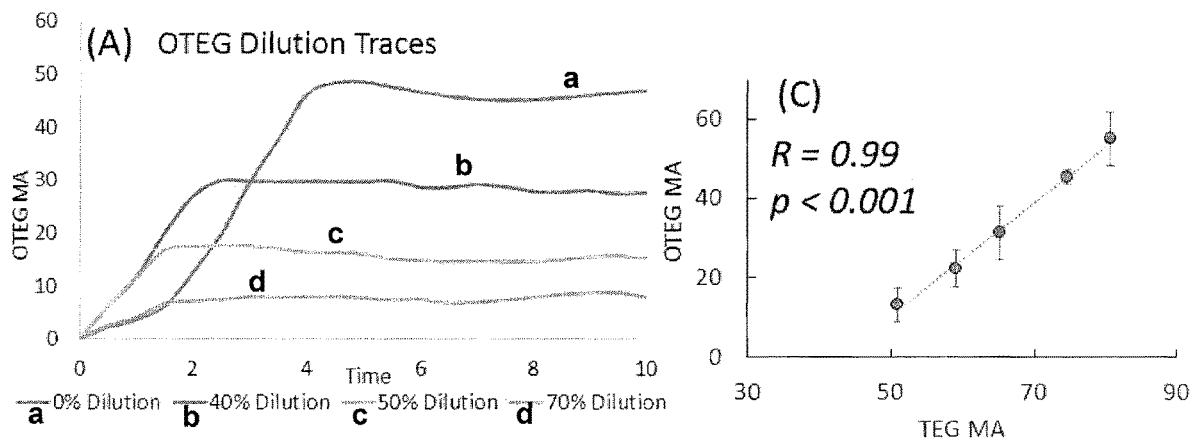
FIG. 9C
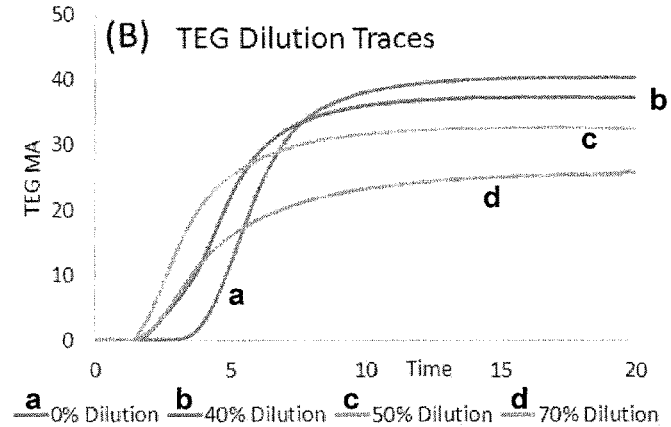
FIG. 9B

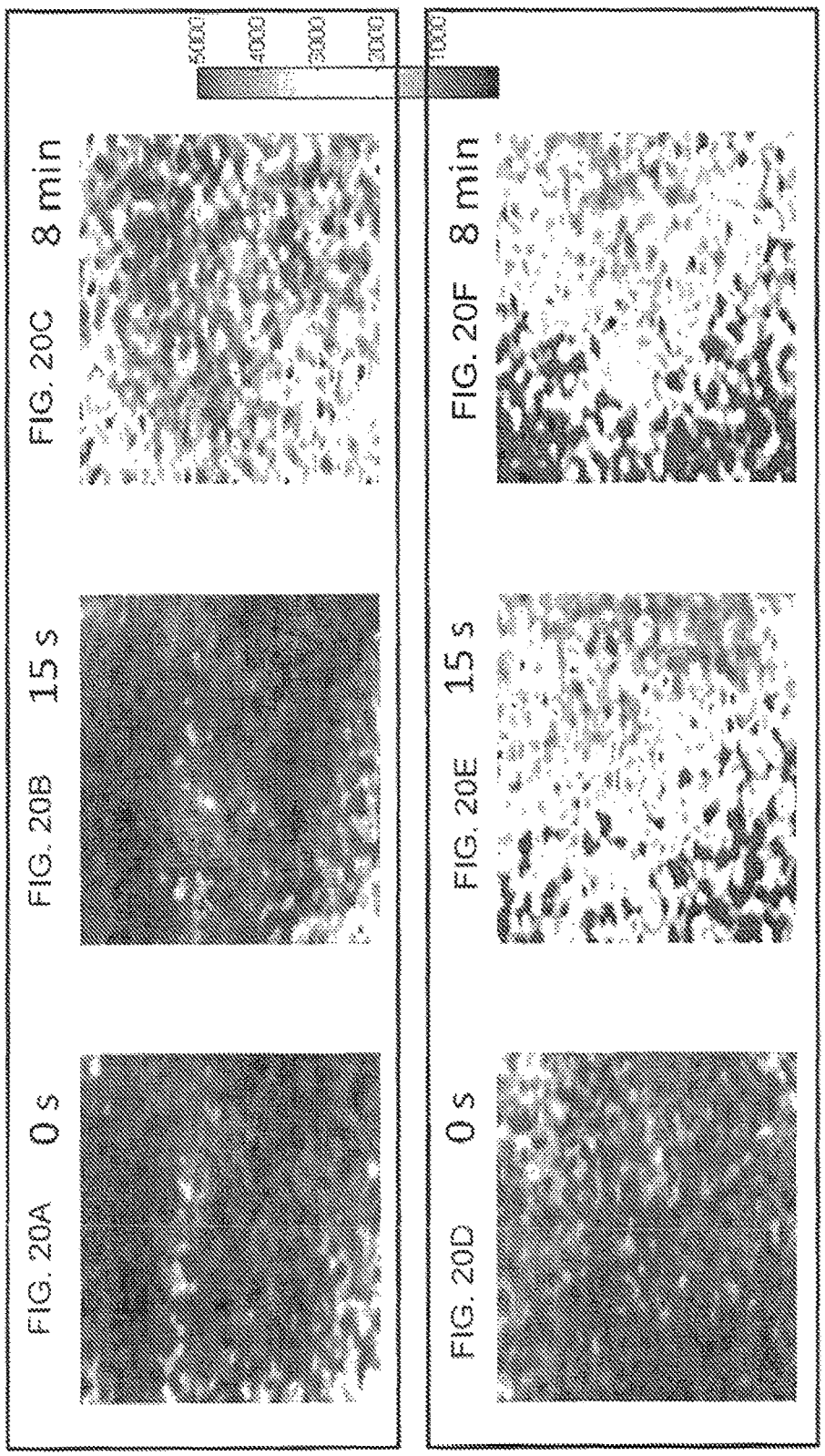

OPTICAL THROMBOELASTOGRAPHY SYSTEMS AND METHODS

CROSS-REFERENCE TO RELATED APPLICATIONS

This application represents the U.S. National Stage of International Application No. PCT/US2015/033464, filed Jun. 1, 2015 which claims the benefit of U.S. Provisional Application Ser. No. 62/005,216, filed on May 30, 2014, both of which are incorporated herein by reference for all purposes.

TECHNICAL FIELD

The present invention relates to systems and methods of monitoring of coagulation of blood and, in particular, to a hand-held multi-functional optical blood-coagulation sensor operable at a point-of-care to provide real time simultaneous assessment of at least clotting time, clot formation rate, clot strength, and platelet function.

BACKGROUND

Impaired blood coagulation or coagulopathy is a frequent cause of bleeding and thrombosis following acute trauma and surgery, and is the number one cause of in-hospital preventable death. Multiple factors including the depletion of clotting factors, impaired platelet function and the systemic activation of fibrinolytic pathways contribute to the development of coagulopathy. To manage defective coagulation, blood components are transfused to correct bleeding abnormalities, whereas, anti-coagulant or anti-platelet agents are administered to correct thrombotic conditions. Inadequate therapy can lead to blood loss and affect the performance of organs and acute thrombotic events, while over-transfusion or overuse of anti-thrombotic agents can exacerbate bleeding. In order to achieve optimal outcome and save lives, the early identification of coagulation defects and frequent coagulation monitoring during therapy is essential.

Similarly, millions of patients worldwide receive oral anticoagulant therapy to prevent and treat arterial and venous thromboembolic events, the world's leading cause of mortality. Despite their effectiveness in lowering the risk of acute thrombosis, oral anticoagulants if inadequately monitored, can cause dangerous blood loss and organ failure. Due to numerous drug interactions, underlying comorbidities and the variability of dose response among patents, effective anticoagulation management is often challenging. As a result, patients require frequent laboratory testing of blood coagulation status to ensure accurate and safe anticoagulant dosing. Furthermore, laboratory-based anticoagulation testing is time-consuming and expensive, and provides insufficient information for effective anticoagulant dosing, while placing a huge burden on health-care costs. It is estimated that over 8 million visits are made annually to primary care service providers in the United States for anticoagulant dosing alone, and the service load for anticoagulation management is expected to increase by five-fold over the next decade, imposing an enormous health-care challenge.

Unfortunately, blood tests in the laboratory environment are ineffective in the context of rapidly changing coagulation conditions in critically ill and injured patients. Furthermore, due to the lack of tools available to clinicians for detecting coagulation defects rapidly at the bedside, there are often delays in managing bleeding and thrombosis, increasing the risk of death by 40%. Together, these factors underscore the dire unmet need for routine home-monitoring (at the point-of-care, PoC) of blood-coagulation status to advance the quality of care for patients.

SUMMARY

Embodiments of the invention provide a cartridge for optical analysis of a blood sample. The cartridge includes an inlet configured to receive the blood sample; and a plurality of analysis chambers in fluid communication with said inlet. Each analysis chamber is selectively loaded with a corresponding blood coagulation activator arranged to interact with the blood sample and receive light incident onto said analysis chamber. The plurality of analysis chambers is oriented such that light, received by the blood sample contained therein, is scattered towards an optical detection unit in optical communication with said analysis chambers to measure at least one parameter of coagulation of the blood sample, a blood platelet aggregation characteristic, and prothrombin time.

Embodiments of the invention also provide a system for optical analysis of a blood sample. The system contains a cartridge including i) an inlet configured to receive the blood sample; and ii) a plurality of analysis chambers in fluid communication with said inlet, each analysis chamber selectively loaded with a corresponding blood coagulation activator arranged to interact with the blood sample and receive light incident onto an analysis chamber from the plurality. The system further includes a data acquisition portion with an optical detector unit. The optical detector unit is configured such as to receive light, that has been delivered into an analysis chamber and that has interacted with a portion of the blood sample contained therein, and to acquire from the light optical data representing scattering of said light by multiple light-scattering events within the portion. The system additionally includes a programmable processor operably connected to the optical detection unit and programmed to calculate, from said optical data, at least one parameter of coagulation of the blood sample, a blood platelet aggregation characteristic, and prothrombin time.

Embodiments of the invention also provide a method for optical analysis of a blood sample with the use of an optical system. Such method includes steps of i) acquiring, with an optical detector unit of the system through an optical port of a removable cartridge containing the blood sample, optical data representing time evolution of a light scattering from particles of a portion of the blood sample contained in an analysis chamber of the cartridge, where the analysis chamber is loaded with a selected blood coagulation activator; and ii) determining a platelet aggregation characteristic based on an autocorrelation function derived from acquired optical data. In one implementation, at the step of determining, the characteristic of platelet aggregation is determined as a function of concentration of the selected blood coagulation factor. In a related embodiment, the determination of the platelet aggregation characteristic is carried out in whole blood and/or in plasma.

Embodiments of the invention additionally provide a related method for optical analysis of a blood sample with the use of an optical system. The method includes the steps of i) acquiring, with an optical detector unit of the system through an optical port of a cartridge, optical data representing time evolution of a light scattering from particles of a portion of the blood sample contained in an analysis chamber of the cartridge, the analysis chamber being loaded with a selected blood coagulation activator; ii) determining a size of said particles based on an autocorrelation function derived from acquired optical data; and iii) calculating, with a programmable processor, a value of mean square displacement (MSD) of the particles based on acquired optical data.

BRIEF DESCRIPTION OF THE DRAWINGS

The invention will be more fully understood by referring to the following Detailed Description of Specific Embodiments in conjunction with the generally-not-to-scale Drawings, of which:

FIG. 8A: Increasing aggregate radius, a, of polystyrene beads (rad=1.5 μm) caused by adding $MgCl_2$ salt is detected by OTEG. Aggregate size was related with salt concentration, confirmed by other reports. FIG. 8B: In human whole blood, OTEG detects a 5-fold and 2.5-fold increase in aggregate size with addition of 10 and 5 μM ADP relative to blood without ADP (control). A small increase in aggregate size in the control sample (no ADP) is likely caused by RBC sedimentation.

FIGS. 9A, 9B, 9C present plots demonstrating the capability of (A)OTEG to quantify changes in MA (FIG. 9A) that is equivalent to the capability of TEG (FIG. 9B). Normal human blood samples are serially diluted with saline to cause dilution-dependent changes in MA. FIG. 9C: Strong correlation between OTEG and TEG MA values.

FIGS. 20A, 20B, 20C, 20D, 20E, and 20F provide 2D maps of platelet aggregation and aggregate size in a small volume of plasma.

DETAILED DESCRIPTION

Figure 1:
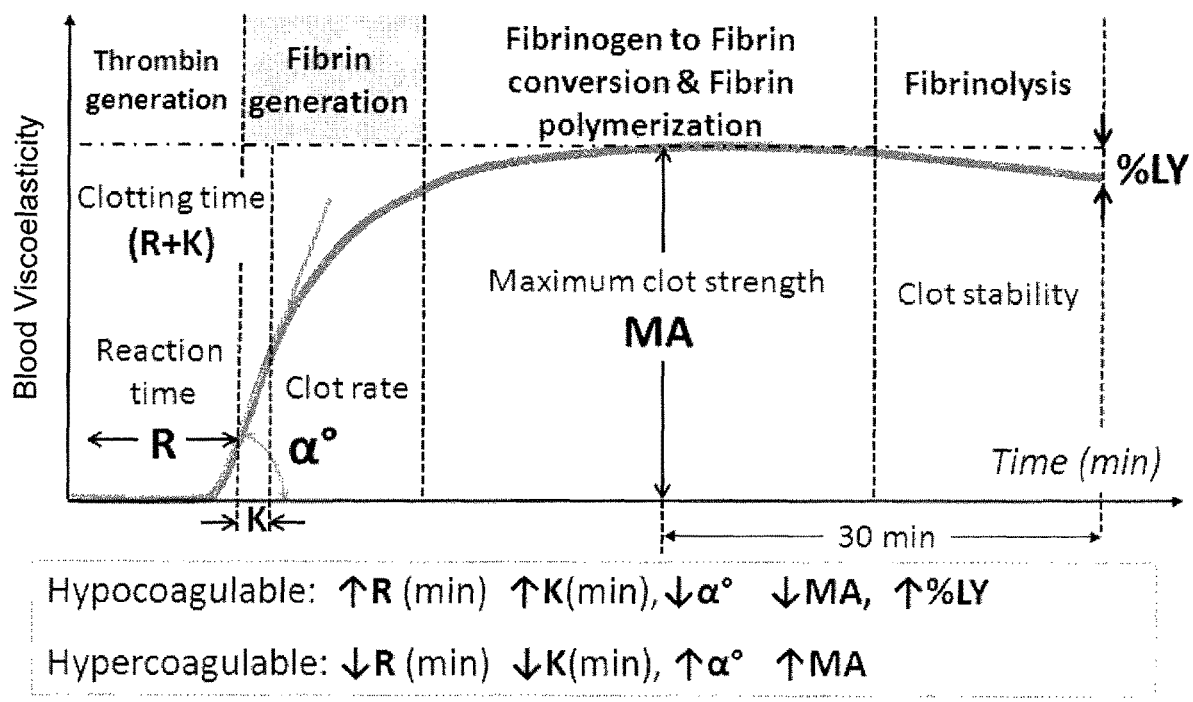
FIG. 1 is a plot of a whole-blood viscoelasticity trace, permitting assessment of the entire coagulation process. Relevant parameters derived from the trace provide information on reaction time for thrombin generation (R), clotting time (R+K), rate of fibrin cross-linking ($\alpha$), clot stiffness (MA) proportional to fibrinogen levels, and clot stability (% LY) to detect hyperfibrinolysis.

Coagulopathy is present in over 25% of major wounds due to blunt and penetrating injuries. If coagulation impairments can be recognized rapidly after severe injury, prompt and optimal intervention can be initiated, which is crucial in saving lives. The normal coagulation process, termed hemostasis, is the body's defense mechanism against uncontrolled bleeding and involves an intricate interplay between platelets, red blood cells (RBCs) and fifteen clotting factors. Coagulation defects may lead to hypo-coagulable states causing prolonged bleeding, or may manifest as hypercoagulable states that can result in potentially fatal complications such as deep vein thrombosis and pulmonary embolism. Acute tissue injury and systemic hypotension caused by severe trauma may trigger coagulopathy via the elevation of activated protein C, factor consumption, platelet dysfunction and the activation of fibrinolytic pathways, causing hemorrhage. Subsequently, these patients may be at risk of later developing life-threatening pulmonary emboli secondary to hypercoagulable states. Therefore, during hemostasis management, clinicians routinely walk a thin line to maintain the delicate balance between bleeding and coagulation.

Depending on the type of coagulation defect, bleeding disorders are treated by rapidly transfusing packed red blood cells (pRBC), plasma, platelets, fibrinogen and clotting factor concentrates, or with anti-fibrinolytic drugs; and thrombotic states may be managed with anti-coagulant or fibrinolytic agents. Since, each coagulation defect necessitates very different therapeutic strategies, the prompt identification of coagulopathic patients and accurate diagnosis of the underlying coagulation defect is essential. Inadequate therapy can cause life-threatening blood loss and organ failure, while over-transfusion can aggravate bleeding via the dilution of clotting factors. The staggering influence of impaired coagulation on mortality in wounded warfighters thus underscores the acute need for timely coagulation monitoring at the point of care, to identify patients at elevated risk of bleeding or thrombosis, tailor early intervention and monitor hemostasis during treatment to improve patient outcome.

A number of devices are available for coagulation testing at the point of care (Table 1). Almost all of these devices only measure clotting time (PT and/or PTT), and fail to identify the underlying coagulation impairment. Among the competition, CLIA-waived devices only measure a single metric of clotting time, given by prothrombin time, PT/INR a (see Table 1 captions). Devices that are non-waived or of moderate CLIA complexity add the capability for measuring activated partial thromboplastin time (PTT). Other devices (PFA 100, VerifyNow) solely measure platelet aggregation to assess platelet dysfunction that often occurs in acutely injured patients. There is yet no single device that provides the full suite of coagulation tests that are required to identify the complex coagulation defects that accompany acute battlefield trauma. As a result, a battery of laboratory tests is required to evaluate all of the relevant coagulation parameters: PT, PTT, clot formation rate, fibrinogen level, fibrinolysis, D-dimer levels and platelet function. Unfortunately, given slow test results (1-2 hrs), conventional coagulation tests are unreliable in the context of rapidly evolving coagulation conditions in severely injured patients and poorly correlate with clinical outcome. The only instruments available to-date for multi-parameter coagulation profiling in whole blood are TEG and ROTEM, both of which involve mechanically stirring blood in a cup and measuring clot viscoelasticity during clotting.

TABLE 1

Point-of-care coagulation testing devices up to date.

| Mode of Operation (Manufacturer & Model) | PoC USE | CLIA Status | Tests Performed | Instrument Cost | Disposable Cost |
|---|---|---|---|---|---|
| Impedance/Amperometric (Roche CoagChek ©, Alere INRatio ©) | yes | waived | Clotting time (PT) | $1,000-2,000 | $5 (PT only)+ |
| Electrogenic (Abbott iStat ©) | yes | non-waived | Clotting time (PT & PTT) | $11,000 | $5.50 (per PT & PTT test)+ |
| Mechanical/MEMS (ITC Hemochron ©, Microfisk CoagMax ©, Medtronic ACT ©) | yes | non-waived/ moderate | Clotting time (PT & PTT) | $5,000-$8,000 | $11.50 (per PT & PTT test)+ |
| Micromechanical (CoaguSense) | yes | waived | Clotting time (PT) | $1,000 | $6 (PT only)+ |
| Optical (IL GEM PCL ©, Helena Cascade ©) | yes | non-waived | Clotting time (PT) | $5,000 | na (volume dependent)+ |
| Aggregometry (optical/shear) (VerifyNow ©, PFA 100) | yes | non-waived | Platelet function | $8,000 | $60 (per test) |
| Mechanical torque (Haemonetics TEG ©, TEM International ROTEM ©) | No (requires 0.5-1 mL blood) | non-waived | Clotting time (PT), clot formation rate, clot strength (fibrinogen), Fibrinolysis, Platelet function | $80,000-$100,000 | $15 (for kaolin based test) $25 (for platelet function) |
| Proposed OTEG device | yes* (~50 µL) | ##waived | Clotting time (PT PTT) clot formation rate, clot strength fibrinogen) Fibrinolysis Platelet function | $1,000-$1,500 | $11 (for all tests)++ |

Table 1 Captions:

(##) While CLIA-waiver is not a requirement for in-hospital point-of-care use, it will open the unique opportunity in the future to extend OTEG for coagulation testing at the point of injury, during transport and in austere military field settings. Therefore, in the current application, device development will be conducted consistent with CLIA waiver standards.

(+) Disposable costs are for per PT or PTT tests, therefore total disposable cost for clotting time measurement alone is twice the cost listed.

(++) In contrast, OTEG provides multi-parametric measurements of at a low cost of $11 per disposable. PT and PTT assess clotting time via the extrinsic and intrinsic coagulation pathways, and both metrics are often tested.

Whole blood viscoelasticity testing using TEG and ROTEM provides comprehensive information on all aspects of the coagulation cascade and has proven to be superior to conventional coagulation tests in monitoring trauma-induced coagulopathy (FIG. 1). However, a major drawback is that TEG and ROTEM are large, expensive, difficult to operate and require cumbersome sample preparation, which severely limits their adoption for point of care use. Alternatively, surface acoustic wave (SAW) and MEMS devices are being investigated for viscoelasticity testing. However, due to complexities of precise fabrication and quality assurance, these devices are yet unavailable for clinical use. Other sono-rheometric approaches measure the mechanical response of blood to acoustic perturbation and require complex electronics with adaptive feedback to modulate the acoustic force above the noise threshold but below levels that induce fibrin disruption. Magnetoelastic sensors are recently shown to enable measurement similar to TEG, but the bulky instrumentation needed to emit a magnetic flux and detect resonant frequency shifts, may render them unsuitable for PoC use.

General

An embodiment of the OTEG device is configured to measure time-varying laser speckle intensity fluctuations that are intimately related with the viscoelastic properties of clotting blood. Speckle that occurs due to interference of laser light scattered from the tissue sample, is exquisitely sensitive to the Brownian motion of endogenous light scattering particles (such as blood cells), which is in turn influenced by the viscoelastic properties of the medium. The increasing stiffness of blood during the formation of a fibrin clot restricts displacements of light scatterers, eliciting a slower rate of speckle fluctuations. Related art demonstrated that the time constant of speckle fluctuations, $\tau$, is highly correlated with the viscoelastic properties of tissues and provides information on the evolution of whole blood viscoelasticity (see, for example, FIG. 2 of this disclosure; see also FIGS. 1A through 1C and 2A, 2B of WO 2014/100378, the entire disclosure of which is incorporated herein by reference)

Figure 5:
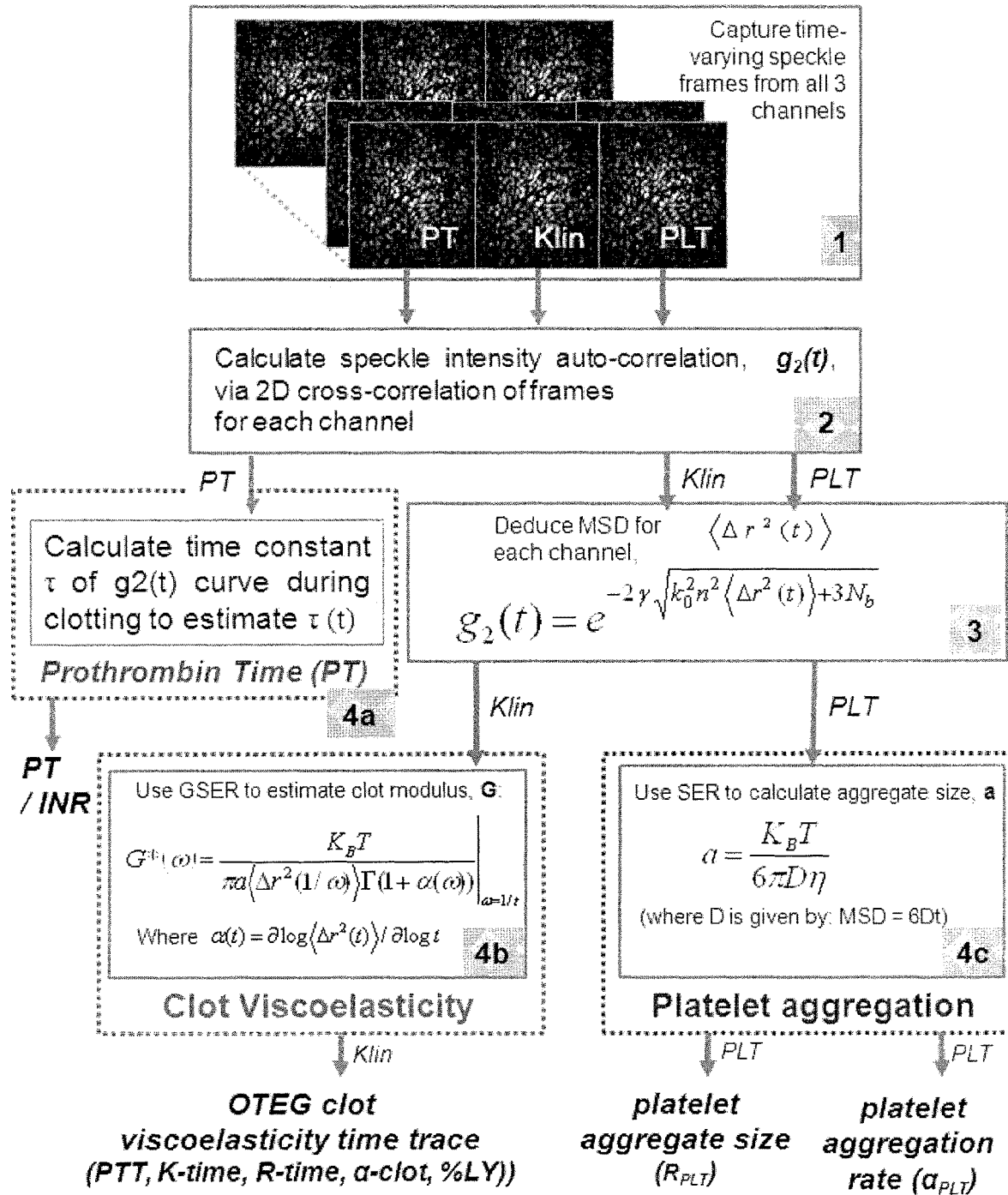
FIG. 5 shows a flow-chart of an OTEG algorithm for real-time processing. Box 1: Time-varying series of speckle frames is captured at a high frame rate from each of the 3 channels. Box 2: Normalized 2D cross-correlation of speckle time series yields the speckle autocorrelation, g2(t) curve, for each channel. Box 3: A simplified closed form equation is used to estimate MSD from the measured g2(t). Box (4a) The duration at which the first order derivative of t-time trace attains maximum is reported as PT. Box (4b) The MSD is substituted in the Generalized Stokes-Einstein Relation (GSER) to yield the viscoelastic modulus of blood. Box (4c) The effective scatter radius, RPLT, is measured from the Stokes-Einstein relation (SER) to yield aggregate size in unclotted blood spiked with a platelet agonist.

While $\tau$ provides an indirect estimate of viscoelasticity, the quantity that defines the viscoelastic behavior of materials is the viscoelastic modulus, G. We have established that the viscoelastic modulus can be accurately quantified from laser speckle fluctuations during coagulation, and G values measured during clotting bear close correspondence with standard mechanical testing and TEG (see discussion in WO 2014/100378 related to FIGS. 8A, 8B, and 12A through 12F). Furthermore, because measurements are based on optical phase shifts of scattered light caused by nanometer-scale particle displacements, the OTEG methodology is exquisitely sensitive to minute viscoelasticity changes during clotting, permitting detection of early micro-clots in less than a minute (FIG. 5 of WO 2014/100378).

As will become apparent from this disclosure, embodiments of the invention possess required accuracy to quantify fibrinolysis equivalent to TEG. Further implemented was the capability for quantifying platelet aggregation in a drop of blood to assess platelet function, a highly relevant parameter required to inform transfusion needs during the early onset of trauma-induced coagulopathy. These studies demonstrated that platelet aggregate size measured by calculating mean square displacements of aggregating platelets from laser speckle fluctuations closely corresponds with laboratory-based light transmission aggregometry (LTA) measurements. Overall, embodiments of the present invention establish the capability for robust quantification of multiple coagulation metrics: clotting time, clot formation rate, clot strength (related to fibrinogen), fibrinolysis, and platelet function with the use of a drop of blood.

Example of a Hand-Held OTEG Device.

Figure 3:
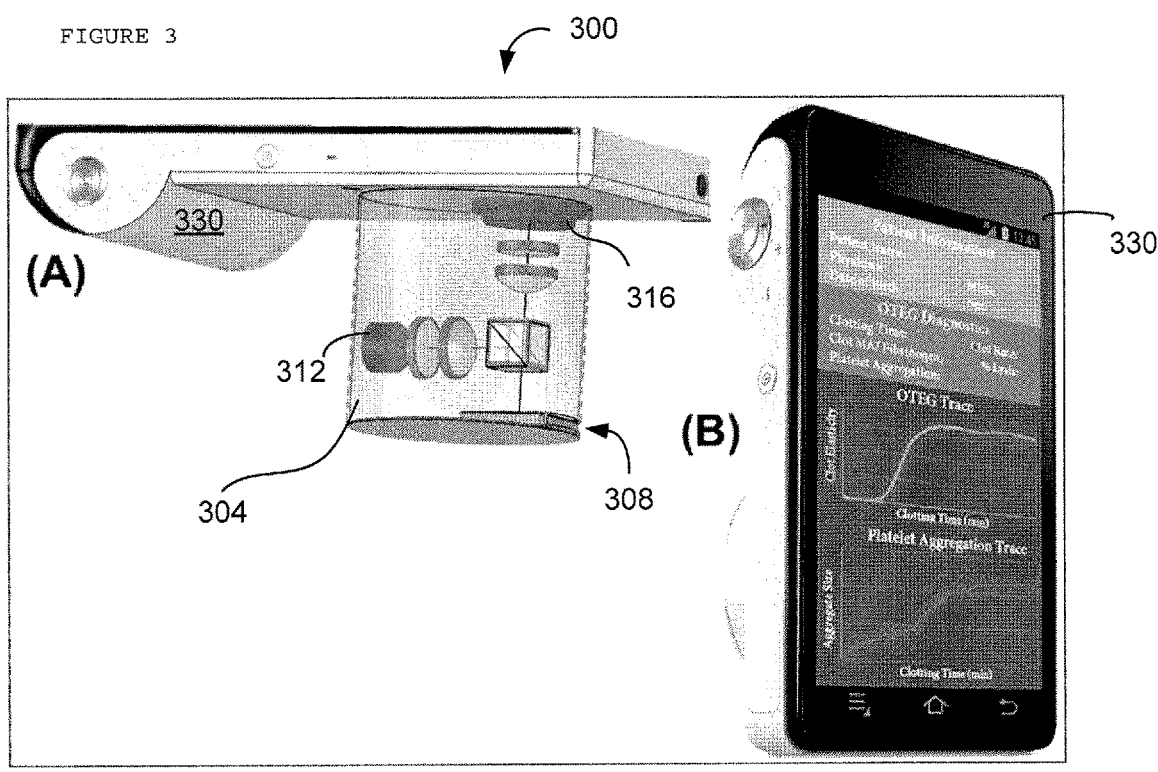
FIGS. 3A, 3B, 3C illustrate schematically perspective views and an opto-electronic scheme of an embodiment of the optical thromboelastographer device according to the invention.
Figure 3:
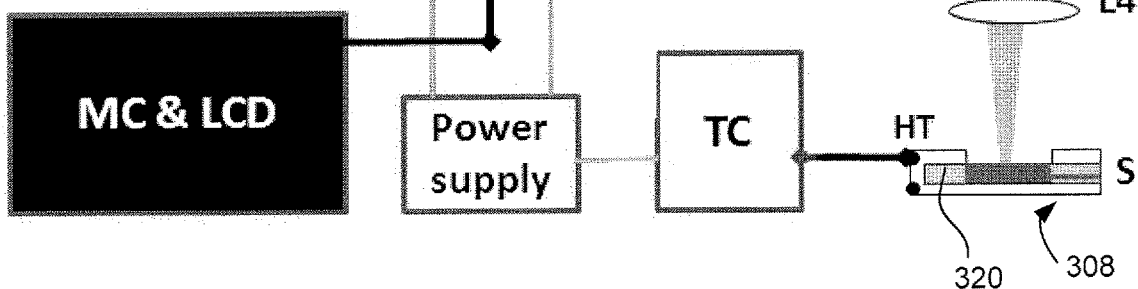

An embodiment 300 of the optical thromboelastographer battery-operated device structured according to the idea of the invention is illustrated with the use of schematic diagrams of FIGS. 3A, 3B, 3C. An embodiment includes an assembly containing a housing unit 304 that hosts a cartridge or sample-holding unit 308, configured to me removably inserted into the unit 304. The unit 308 has a dedicated container for a sample medium scattering light incident thereon from the coherent light source 312 (a laser diode at 690 nm, for example) that gives rise to a laser-speckle collected with an optical detector 316 from the active read-out area of the cartridge, as discussed below.

The optical module may be assembled within a cylindrical housing 304 (2"×2") interfaced with a CMOS camera via a standard C mount. The CMOS camera (such as Samsung Galaxy camera, for example) is chosen to achieve high frame rates (up to 500 fps) required for OTEG, and, in one implementation, is integrated with a quad-core processor (such as Tegra 4) and a 5" LCD display. Speckle pattern acquisition and OTEG processing routines (detailed below) are performed in real-time by exploiting parallel computing capabilities. OTEG data is stored on on-board memory for transfer and analysis as needed.

A cartridge slot is machined within the front face of the OTEG housing to secure the cartridge unit 308 in place on top of a 1" temperature controller (for example, a custom heated plate). A temperature-controlled cartridge nest is designed to lock in the cartridge, mix coagulation reagents and maintain a 60 µL blood sample at a specified temperature. The cartridge nest incorporates actuated miniature pistons or pins that serve to control pneumatic pumps transporting and positioning blood sample(s) within multiple operationally-parallel read-out channels of the cartridge unit, as discussed below.

A major practical limitation of conventional TEG measurements is the requirement for cumbersome blood sample preparation that involves pipetting and mixing precise volumes of blood, coagulation activators and reagents prior to testing. As a result, TEG is often relegated to a central laboratory setting causing delays in accessing test results. To address these limitations of the existing TEG modality, in one implementation the cartridge 308 includes a small chamber (for example, several millimeters in diameter) constructed within a 1-2 mm thick, blood-compatible silicone base, optionally sandwiched between two optically clear polycarbonate films (with thicknesses of a part of millimeter, for example 0.15 mm). Non-limiting examples of the cartridge 308 are further detailed below.

To operate the device, a few drops of whole blood are placed within the cartridge (V<100 µL) secured in place within the cartridge slot. To optionally permit direct comparison of OTEG coagulation parameters with TEG, standard coagulation activators and agonists (e.g., kaolin, ADP) are titrated, preloaded within the cartridges and provided for use. Accordingly, the cartridge 308 may include a base substrate 320 defining a void and having a first surface with an aperture providing access to such void. The cartridge 308 may further include a superstrate or upper cover 324 juxtaposed with the first surface over the aperture to form a closed chamber including the void such as to prevent access to said chamber through the aperture. Since the laser speckle information, from which the OCS device is determining the relevant blood-coagulation parameters, is susceptible to external vibrations, an embodiment of the device optionally incorporates a vibration-isolating platform (not shown) operable to compensate for a relative movement between the base substrate and the housing unit. Time-averaging and Fourier domain filtering of $g_2(t)$ curves can be optionally implemented to remove the influence of residual instabilities. The embodiment 300 further includes a hand-held data-processing unit 330 that includes programmable electronic circuitry in operable communication with the detector 316. The housing 304 and the data-processing unit 330 are removably and operably connected to one another through, for example, a C-mount.

Examples of Embodiments of Disposable Cartridge for OTEG Device

A major limitation in conventional TEG is the requirement for cumbersome blood sample preparation that involves pipetting and mixing precise volumes of blood, coagulation activators and reagents prior to testing. As a result, TEG is often relegated to a central laboratory setting causing delays in accessing test results. Embodiments of the present invention include an inexpensive disposable blood cartridges, operably compatible with the OTEG device that draw and mix 60 μL of blood or blood constituent into a microfluidics chamber pre-loaded with coagulation activator (s).

Figure 4A:
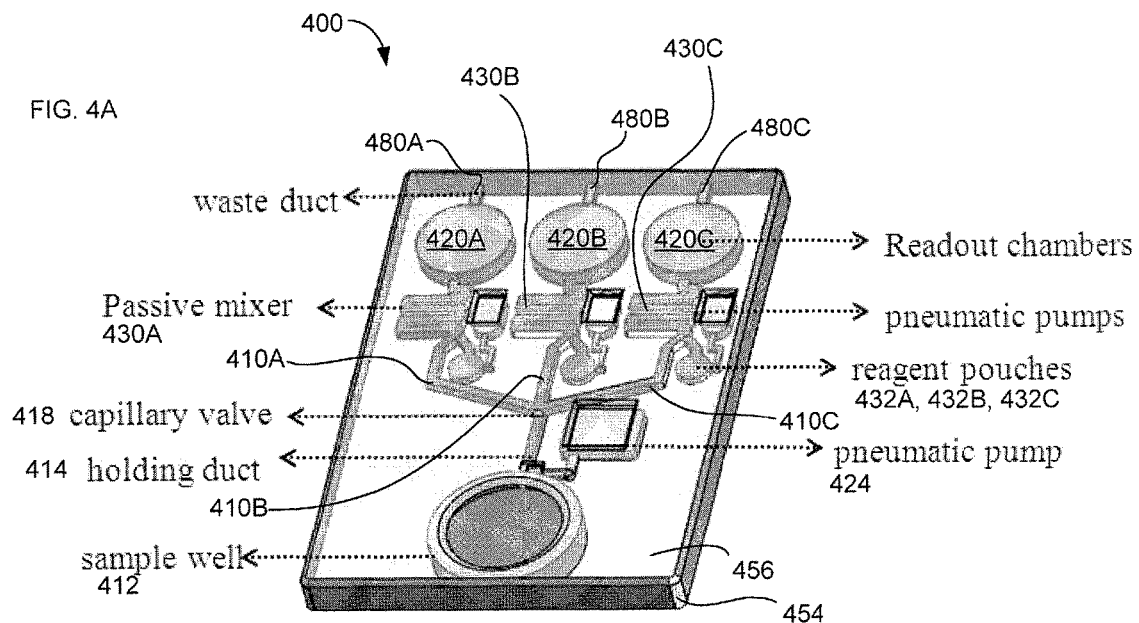
FIG. 4A is a schematic diagram of a cartridge of the hand-held OTEG device structured according to an embodiment of the invention.
Figure 4B:
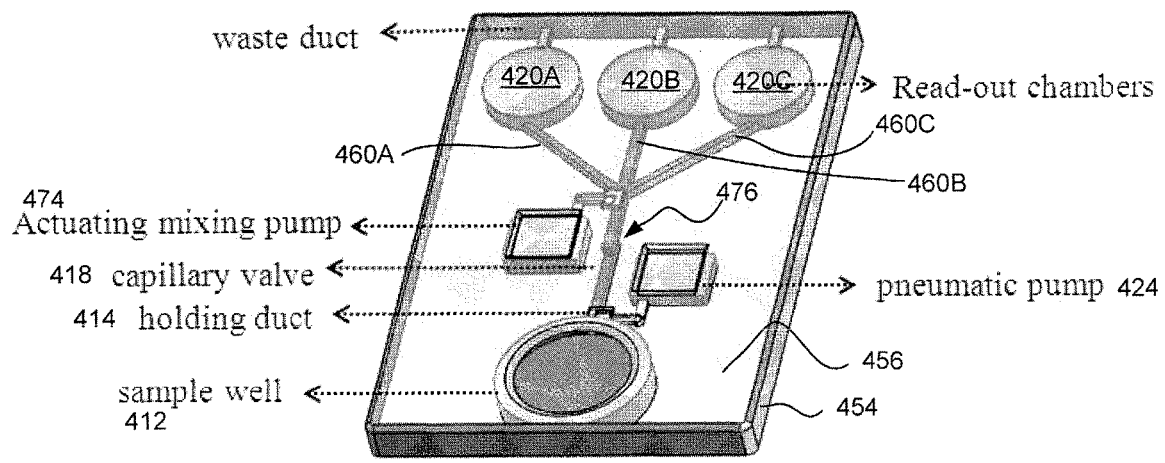
FIG. 4B is a schematic diagram of a cartridge of the hand-held OTEG device structured according to a related embodiment of the invention.

Disposable (with dimensions of 1.0×2.5 $cm^2$ or thereabouts) single-use cartridges—such as two examples of embodiments 400, 450 shown schematically in FIGS. 4A and 4B—are fabricated using an injection-molded plastic base 404, 454 and a optically clear polycarbonate cover 406, 456 providing an optical port through which light incident onto the cartridge reaches the inside volume(s) of the individual chambers and configured as a fluid seal preventing leakage of contents of each of the chambers outside of the chambers. Each of the embodiments is shown to have three channels (such as channels 410A, 410B, 410C; 460A, 460B, 460C) to simultaneously measure PT (the PT channel being preloaded with tissue factor), clot viscoelasticity (the Klin channel being preloaded with kaolin), and platelet aggregation (the PLT channel being preloaded with ADP agonist and anticoagulant, calcium citrate). Data acquired with the use of the kaolin-loaded channel provides OTEG viscoelasticity curves (the dependence of OTEG amplitude on clotting time, for example) that are equivalent to standard TEG read-outs to enable simultaneous multi-parametric measurement of PTT (Ktime), clot formation rate (α) and time (K), clot strength (MA related to fibrinogen), % LY (fibrinolysis). The platelet channel of the cartridge is configured to facilitate platelet aggregometry testing and provide information on aggregate size and platelet aggregation rate (detailed below, in reference to FIGS. 8A, 8B, 17A, 17B, 19A, 19B). In operation, all three channels are simultaneously illuminated through the cover 406, 456 with light L (for example, with a collimated laser beam of about 1 cm in diameter; not shown), and time-resolved speckle patterns are acquired at the same time from all three channels with an optical detection unit, thereby enabling measurement of all of the above parameters within a single disposable cartridge embodiment. Mechanisms for active and passive mixing of blood with reagents within the embodiments 400 and 450 are discussed below.

In both active and passive designs, a blood drop is introduced in the sample inlet 412 (volume V of about 60 μl) and capillary forces propel the blood drop into a sample holding duct 414. The walls of this duct may be plasma-air treated to enhance their surface energy and boost the capillary forces for a faster loading of the sample.

In both designs, the sample holding duct terminates with a capillary valve 418 that prevents the flow of blood towards imaging (read-out) chambers 420A, 420B, 420C. This capillary micro-valve is formed by creating a step in the channel passing thought it, and a capillary bore is introduced at the interface of the two levels of the stepped channel. A meniscus of blood is formed at the perimeter of the bore, which meniscus is pinned in place due to the abrupt change of the channel geometry. A pneumatic pump 424 (such as one built with a membrane overlaying a small air sac) operates to move the sample beyond the valve 418 and towards the three chambers 420A, 420B, 420C (V=20 μL each) after the cartridge has been inserted into the OTEG device. The combination of the capillary micro-valve and the corresponding pneumatic pump forms an effective fluid switch, activatable in response to an input provided by the user. Once the cartridge is inserted and locked in place within the cartridge nest and temperature is stabilized at, for example, 37° C., the 424 pump's membrane is compressed by a pin in the nest, generating a burst of pressure that forces blood to fill the readout imaging chambers.

In the passive fluidic mixing configuration of the embodiment 400, three small pouches 426A, 426B, 426C that contain metered aliquot of the three different liquid reagents are placed distal to the capillary valve 418 at the entrance port of each passive micro-mixer channel 430A, 430B, 430C. Small pneumatic pumps 432A, 432B, 432C, with which the pouches are respectively operably fluidly connected, operate to provide the driving force for the reagent to break through the valves. Reagents within each pouch are displaced via designated pistons incorporated within the cartridge nest that push on the pump membranes to force reagents into the blood stream in each channel. Passive micro-mixers 430A, 430B, 430C are micro-machined within each channel to allow the blood and reagent streams to flow laminarly through the mixers. In one implementation, the mixers are composed of a tortuous channel with porous inner walls and the constantly changing flow direction induces a self-folding effect which results in uniform mixing of blood specimens with reagents.

In the active fluidic mixing configuration 450, on the other and, a pneumatically-actuated mixer pump 474 is connected to the entrance duct 476 just before it branches into three channels 460A, 460B, 460C. These 3 channel branches terminate, respectively, in the read out chambers 420A, 420B, 420C preloaded with measured aliquots of reagents. Once the cartridge is locked within the cartridge slot of the OTEG device, a small modulating piston of the mixing pump 474 oscillates the diaphragm of the mixing pump (for example, at frequency of a few Hz, say, 3 Hz, over 5 to 10 seconds or so). The modulation of air pressure pushes and pulls blood between the imaging chambers and the three channels to accomplish thorough mixing of blood with the reagents within each chamber. To avoid back flow of blood from the channels 460A, 460B, 460C into the main X76 duct and mixing among the contents of the channels, the entrance to the duct is treated, in one implementation, with a hydrophobic material.

In both designs 400 and 450, three waste ducts 480A, 480B, 480C are respectively fluidly attached to the imaging (read-out) chambers to collect excess of blood samples. The waste ducts may be further fluidly connected to a common fluid outlet.

It is appreciated, therefore, that an embodiment of the hand-held OTEG device of the invention provides a fluid meter system that includes, in general a sample-holding unit or cartridge. The sample-holding unit includes fluid inlet and fluid outlet; a sample chamber fluidly connected with the fluid inlet through an inlet capillary channel; and multiple read-out chambers, each in fluid communication with the sample chamber through a fluid switch, each having an optical-transparent surface. The sample-holding unit further includes outlet ducts fluidly connecting the respective multiple read-out chambers with the fluid outlet. The fluid switch includes a fluid switch channel dimensioned to have a step therein, the step being dimensioned to prevent propagation of fluid from the sample chamber in absence of an external input applied to the fluid switch channel. A fluid meter system of the invention may additionally include a fluid switch pump in operable communication with the fluid switch channel and the sample chamber, such fluid pump being in fluid communication with the fluid switch channel through a capillary bore located at an interface at said step.

In one implementation, the fluid switch channel includes a capillary having an input end and a terminus, and a read-out chamber channel an input end of which is fluidly connected to the capillary at the terminus. In a specific case, such read-out chamber from the multiple read-out chambers is connected to a distal end of the read-out chamber channel, and the sample chamber is connected to the input end of the capillary, and the fluid meter system may additionally contain a fluid mixing pump fluidly connected with the fluid switch channel at a point located between the sample chamber and the read-out chamber in question, as well as a piston corresponding to and governing an operation of the fluid mixing pump. Such point of connection is along a length of the capillary, while the read-out chamber in question contains a reagent aliquot. Alternatively, such point of connection may be located between the terminus and the read-out chamber, while the system additionally includes a reagent chamber between the point of connection and the fluid mixing pump, and while the reagent chamber contains a reagent aliquot. The read-out chamber channel may include a twisted portion having a porous inner wall.

In a related embodiment, the fluid meter system of the invention additionally contains an optical data acquisition system configured to receive light that has interacted with contents of a read-out chamber and to acquire optical data representing scattering of said light by multiple light-scattering events within the contents; as well as a processor operably cooperated with the optical data acquisition system and programmed to derive, from acquired optical data, a parameter characterizing a time-dependent characteristic of the contents of the read-out chamber. The optical data acquisition system may be configured to receive light, from a source of coherent light that has interacted with the contents of the read-out chamber, while the chamber contains a reagent in fluid communication with the contents, which reagent may be chosen to trigger aggregation of platelets of blood when the contents include blood. Alternatively or in addition, such reagent may be configured to maintain viscosity of said contents unchanged with time. The processor of the fluid meter system is programmed at least to determine a size of the light-scattering particles causing the multiple light-scattering events based on a scattering data derived from the optical data; and to calculate a mean square displacement (MSD) value for the light-scattering particles and a mechanical property of the sample from the optical data.

Alternatively or in addition, embodiments of the invention provide a cartridge for a hand-held OTEG device configured for optical analysis of a blood sample. In one implementation, such cartridge includes an inlet configured to receive the blood sample and a plurality of analysis chambers in fluid communication with said inlet. Each analysis chamber is selectively loaded with a corresponding blood coagulation activator arranged to interact with the blood sample and receive light incident onto said analysis chamber. The analysis chambers are oriented in a body of the cartridge such that light, received by the blood sample in the chambers, is scattered towards an optical detection unit in optical communication with the analysis chambers to have measured at least one parameter of coagulation of the blood sample, a blood platelet aggregation characteristic, and prothrombin time. A parameter of coagulation includes at least one of clotting time, clot viscoelasticity, clot lysis, clot formation time, clot formation rate, and activated partial thromboplastin time. A first analysis chamber from the plurality contains a tissue factor, a second analysis chamber from the plurality contains a coagulation activating agent, and a third analysis chamber from the plurality contains a platelet agonist and anticoagulant. In a related embodiment, the cartridge further comprises at least one optical port providing, in transmission therethrough, optical communication between an ambient medium surrounding the cartridge and volumes defined by the plurality of analysis chambers. The optical port may be structured as a fluid seal sealing an analysis chamber from the plurality of chambers. In addition, the cartridge includes a fluid switch through which each of the analysis chambers and the inlet are in fluid communication. Such switch contains a channel with a step formed in the channel and dimensioned to prevent propagation of the blood sample from the inlet to an analysis chamber in absence of an external input applied to said step. The fluid switch further includes a fluid switch pump configured to apply fluidic pressure to said step through a capillary bore located at an interface of said step. A specific implementation of the cartridge may contain a fluid mixing pump fluidly connected with the fluid switch at a point between the inlet and an analysis chamber, and a piston configured to govern an operation of such fluid mixing pump.

OTEG Device Specifications and Requirements

The OTEG device specifications and performance benchmarks (Table 2) is verified using test phantom materials, polydimethylsiloxane (PDMS), polyethylene glycol (PEG) and glycerol placed within the custom cartridge.

TABLE 2

Benchmark performance metrics for OTEG technology

| Performance Target | Expected value |
|---|---|
| Sample volume | ~60 μL |
| Measurement temperature | 37° C. ± 1° C. |
| Field of View (FOV) | ~ 1.0 cm |
| Measurement depth | ~ 0.5 mm |
| Image transfer rate | 500 MB/s |
| Frame rate | ~500 frames/s |
| Measurement Range | ~0.01 to 500 Pa |
| Measurement sensitivity (smallest detectable change in G) | ~0.01 Pa (based on preliminary studies) (see attached publications) |
| Accuracy | Correlation: $R > 0.7$, $p < 0.05$; & <10% deviation between OTEG and mechanical rheometer $R > 0.7$, $p < 0.05$ for correlation between OTEG and TEG |
| Frequency range of $\omega$ | ~0.01-100 Hz |
| Imaging time per frame | Sample dependent (~1-2 s for softer sample of <1 kPa; ~10 s for stiffer samples ~10 kPa) |

TABLE 2-continued

Benchmark performance metrics for OTEG technology

| Performance Target | Expected value |
| --- | --- |
| Precision/Reproducibility | ~90% |
| Data reporting interval | ~20 s |
| Total reporting time | <1 minute (for PT channel) |
| | <5 minutes (for Klin channel)* |
| | (*fibrinolysis results may take >10-15 min) |
| | <10 minutes (for PLT channel) |

To determine the sensitivity and measurement range of the OTEG device, samples of citrated blood are measured within blood cartridges to evaluate $G(\omega)$ assuming an RBC particle diameter for validation purposes. In all cases, the accuracy and precision of the new OTEG device in measuring the modulus, $G(\omega)$, is evaluated using conventional mechanical rheometry as a reference standard, to confirm less than 10% deviation in measurement. Reproducibility studies are conducted by performing multiple OTEG tests to evaluate intratest variability in normal human samples, and success is defined as <10% deviation in measurement. To validate the capability for platelet aggregate testing, various concentrations of platelet-rich plasma are mixed with whole blood, and aggregate growth (PA) is measured over a range of ADP concentrations. In additional blond samples, OTEG values of samples prepared using standard mixing techniques (used in TEG) are compared with automated reagent mixing enabled by embodiment(s) of FIGS. 4A, 4B.

Methodology of Rapid Quantification and Reporting of Coagulation Parameters.

The approach for recovering multiple blood-coagulation parameters from laser speckle images, configured according to an embodiment of the invention, is outlined in the flowchart of FIG. 5, and the specific details of its implementation described below. Time-varying laser speckle patterns acquired from each of the three PT, Kaolin (Klin), and Platelet (PLT) readout channels of an embodiment of the cartridge of FIGS. 4A, 4B are processed in parallel to quantify prothrombin time (PT), clot viscoelasticity metrics (K, R, α, MA and % LY) and platelet aggregation respectively (box 1 of FIG. 5). For each of the 3 channels, measured are the g2(t) curves via the normalized cross-correlation analysis of the 1st speckle frame with the subsequent time series (box 2 of FIG. 5).

(I) Prothrombin Time:

To measure prothrombin time (PT) the time constant, r, of the temporal speckle intensity autocorrelation curve, g2(t), is calculated at each second for the PT channel (as shown in box 4a of FIG. 5). As previously described in reference to FIGS. 2A, 2B of WO 2014/100378, the duration of time over which the first order derivative of the r time trace attains a maximum value is reported as PT.

Figures 2A, 2B, 2C:
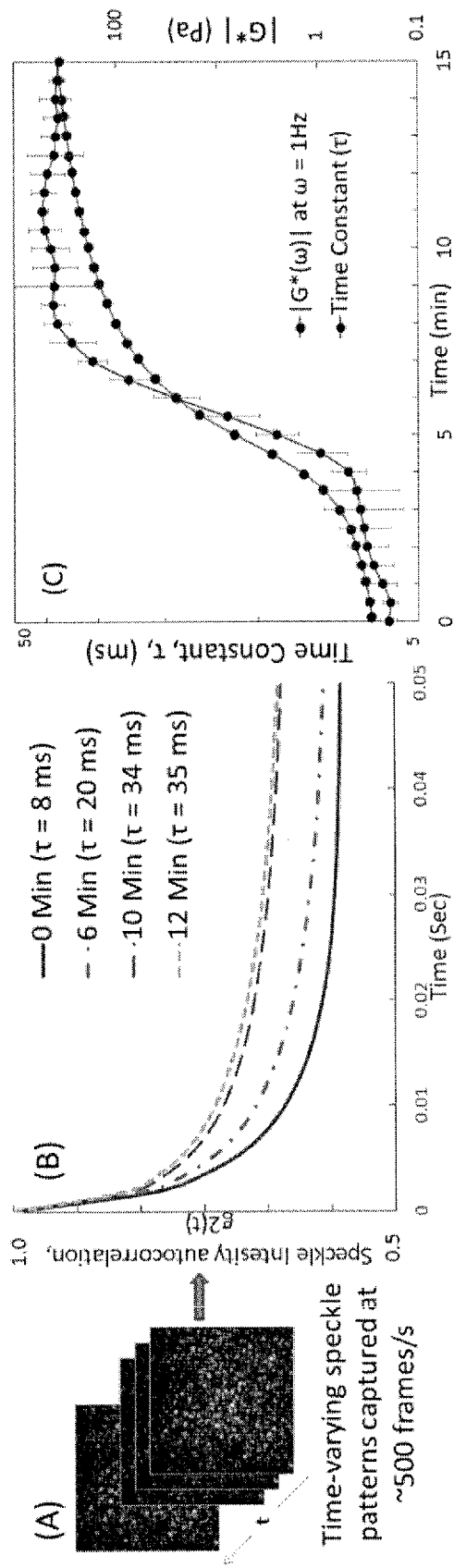
FIGS. 2A, 2B, 2C show laser speckle time series acquired with an optical detector of a device of the invention are analyzed via 2D cross-correlation to calculate speckle autocorrelation, g2(t) curves during clotting. Increasing clot stiffness elicits slower speckle fluctuations corresponding to elevated time constant, $\tau$, that closely corresponds with blood viscoelasticity, G, measured during clotting using a standard ARG2 rheometer.

(II) OTEG Viscoelasticity Trace:

As we noted earlier, the time constant, τ, is intimately linked with the extent of Brownian motion of light scattering particles, in turn related with tissue viscoelasticity (see FIGS. 2A, 2B, 2C herein as well as WO 2014/100378, FIGS. 1A, 1B, 1C and related portions of disclosure therein). While r provides an indirect estimate of viscoelasticity, the quantity that defines the viscoelastic behavior of materials is the frequency-dependent viscoelastic modulus, $G(\omega)$, traditionally measured using a mechanical rheometer. Related art has shown that $G(\omega)$ can also be quantified optically by evaluating the mean square displacement (MSD) of light scattering particles from speckle intensities that fluctuate at frequency, $\omega$, and by using a continuum approximation of light diffusion to describe the MSD-g2(t) relationship. The modulus, $G(\omega)$, can be then estimated from MSD via the generalized Stokes-Einstein relation (GSER). It was subsequently established that the viscoelastic modulus, $G(\omega)$, of clotting blood can be similarly estimated from the MSD derived from reflected laser speckle fluctuations during coagulation. That prior work in now leveraged to quantify the OTEG viscoelasticity trace following coagulation activation using Kaolin (Klin channel) and recover multiple coagulation parameters from laser speckle patterns. The MSD is calculated using the equation in box 3 of FIG. 5, where $Nb=\mu_a/\mu_s$, is the ratio of optical absorption to scattering coefficient of blood. In prior studies, to measure the optical properties of blood from laser speckle patterns, the value of Nb was estimated to be equal to ~0.135, which closely corresponds to published values. Next, the viscoelastic modulus $G(\omega)$ is then calculated via the GSER using previously established mathematical formalisms (box 4b of FIG. 5). Here, the logarithmic slope, $\alpha(t)$, of the MSD is evaluated, and the algebraically-approximated Fourier transform of MSD is obtained from $\alpha(t)$ and substituted in the GSER to quantify $G(\omega)$. This approach, applied to evaluate $G(\omega)$ in biological fluids, produced results closely corresponding to those obtained with mechanical rheometry. See, for example, FIG. 5 and the related portion of the disclosure of WO 2014/100378, discussing the application of this processing scheme to quantify $G(\omega)$ of human blood samples; the results closely mirror mechanical rheometry.

To quantify the absolute value of $G(\omega)$ during clotting, an estimate of the effective particle radius, a, undergoing Brownian motion is needed. Since the parameters, a and $G(\omega)$, are both altered due to platelet aggregation and fibrin clot formation, the accurate estimation of particle size involves complex and bulky instrumentation. These requirements is obviated by measuring, according to an embodiment of the invention, the quantity, $G=aG(\omega')$ at a single frequency $\omega=\omega'$. This quantity represents the viscoelastic modulus scaled by a particle diameter, a. Such strategy confirmed that relative changes in clot viscoelasticity defined by aG, closely follow the results produced not only by mechanical rheometry but also those by TEG while, at the same time, requiring only a short duration of imaging (on the order of 500 ms).

Evaluation of precision and diagnostic accuracy of OTEG measurement in comparison with the those achieved with the use of mechanical rheology has been discussed, for example, in WO 2014/100378 (see, for example, FIG. 6 and the related portion of the disclosure) for the modulus G measured at 100 Hz.

Evaluation of Precision and Diagnostic Accuracy of OTEG Measurement in Comparison with the Those Achieved with the Use of Standard TEG.

At least the following coagulation parameters obtained with the use of OTEG methodology are of interest: reaction time ($R_{OTEG}$), clot formation time ($K_{OTEG}$), rate of clot formation ($\alpha_{OTEG}$), maximum amplitude ($MA_{OTEG}$), and fibrinolysis (% $LY_{OTEG}$).

Based on clinical laboratory diagnosis, multiple de-identified citrated blood samples (N~hundreds) with known or suspected coagulation defects based on clinical diagnoses blood samples are characterized into the following groups: normal, hypo-coagulable, hyper-coagulable, hyper-fibrinolytic and platelet dysfunction. Prior to OTEG testing, anti-coagulation is reversed by calcium substitution. Re-calcified blood are transferred into the OTEG blood cartridge (volume ~60 μL) and secured within the OTEG cartridge slot to begin evaluation. Coagulation parameters measured from each of the multiple cartridge read-out channels are then reported and stored, and the comparison between the performance of OTEG (Kaolin channel) with standard TEG is carried out with the use of the OTEG device of FIGS. 3A, 3B, 3C, 4A, 4B. The following OTEG coagulation parameters are derived: reaction time, $R_{OTEG}$, rate of clot formation defined by $\alpha°_{OTEG}$ and $K_{OTEG}$, and the maximum clot strength given by the maximum OTEG amplitude, $MA_{OTEG}$. In samples that exhibit fibrinolysis, the extent of clot dissolution given by % $LY_{OTEG}$ is recorded by measuring the change in OTEG elasticity a fixed duration after MA is reached (see FIGS. 10A, 10B below).

Figure 6:
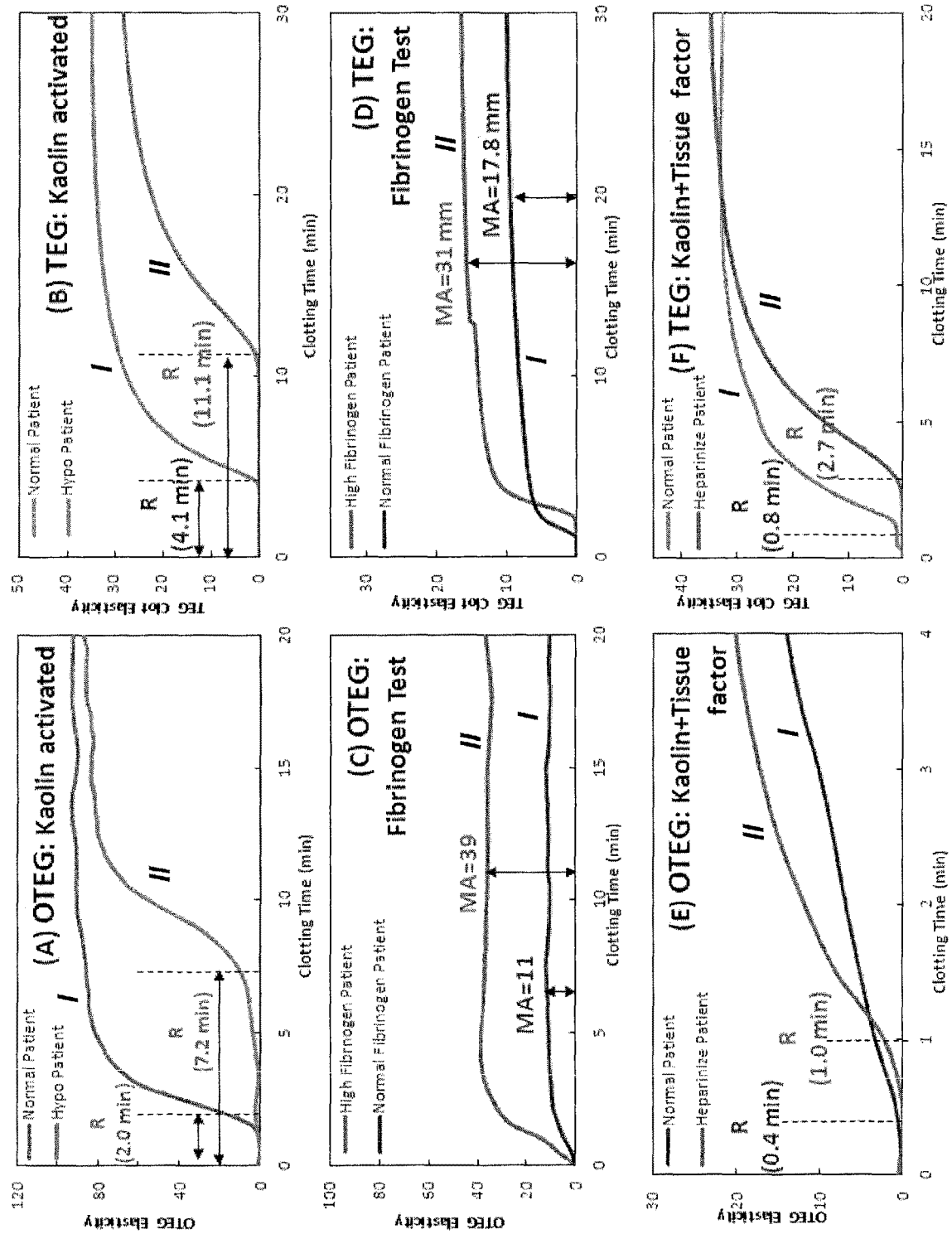
FIG. 6 illustrates the comparison between blood viscoelasticity curves obtained using an OTEG embodiment of the invention (left column, plots A, C, E) and conventional TEG approach (right column, plots B, D, F) using different functional assays.

Notably, preliminary comparison of the OTEG results (obtained with bench-top implementation of the OTEG device) showed a good correlation, see FIG. 6. FIG. 6 (plots A, B, C, D, E, and F) schematically illustrate the results of preliminary studies conducted with the use of the existing bench-top OTEG in comparison with the results of corresponding TEG analysis (used as a standard reference). Normal coagulation status in 3 patients (curves I) is compared with 3 patients with coagulation defects (curves II). Plot A: using standard Kaolin assay, OTEG accurately detects increased R-time and lower clot strength (MA) in hypocoagulable versus normal blood. Plot C: using functional fibrinogen assay, OTEG accurately measures increased clot strength (MA) due to increased fibrinogen levels. Plot D: Adding tissue factor to Kaolin significantly shortens clotting time via activating both the intrinsic and extrinsic pathways and is accurately detected by OTEG as is noted by comparing R-times in plots A and C. In all cases, OTEG results closely correlate with corresponding TEG results shown in plots B, D and F. The results presented in FIG. 6 attest to the fact that an OTEG embodiment of the invention is operable to provide coagulation data similar to those conventionally received with the use of a TEG modality, but optically, using minute sample volumes, within about $\frac{1}{4}^{th}$ of the time, and at a hundredth of the cost associated with the TEG measurement.

Figure 7A:
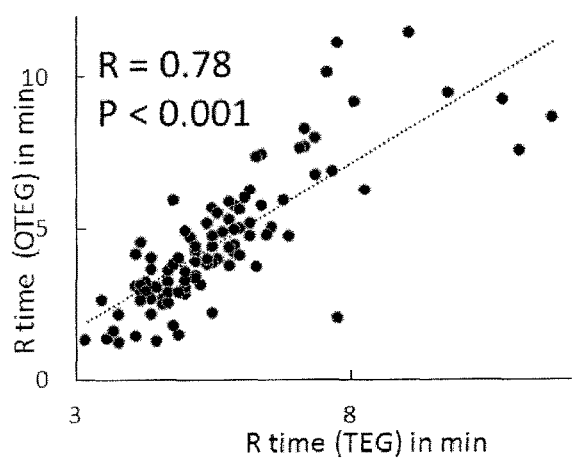
FIGS. 7A, 7B, 7C provide plots demonstrating high-level correlation between the results obtained with a bench-top version of the OTEG device and those procured with standard TEG methodology.
Figure 7B:
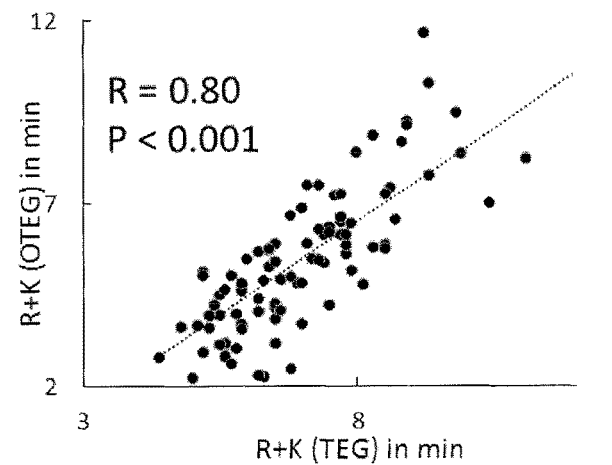
Figure 7C:
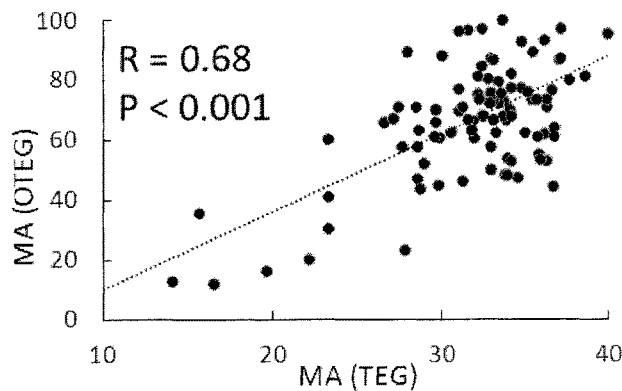

Preliminary studies in 100 normal and coagulopathic patients using the preliminary bench-top version of the OTEG set up, as seen in FIGS. 7A, 7B, 7C, confirmed that OTEG parameters strongly correlate with TEG values. Furthermore, the bench-top implementation of the OTEG system achieved 100% sensitivity and 89% specificity in detecting patients with coagulation defects confirmed by clinical diagnoses.

Evaluation of Sensitivity of OTEG Measurement to Dose-Dependent Coagulation Changes.

For the purpose of evaluating the measurement sensitivity of the embodiment of the OTEG device, previously published protocols for the in vitro modification of blood coagulation status, which have been well-established for TEG validation studies, can be employed (see, for example, Viola F., et al., in Clinica Chimica Acta; international journal of clinical chemistry; 2010, 411, 106-113; see also Haas T. et al., in Anesth. Analg., 2008, 106, 1360-1365).

Figure 10A:
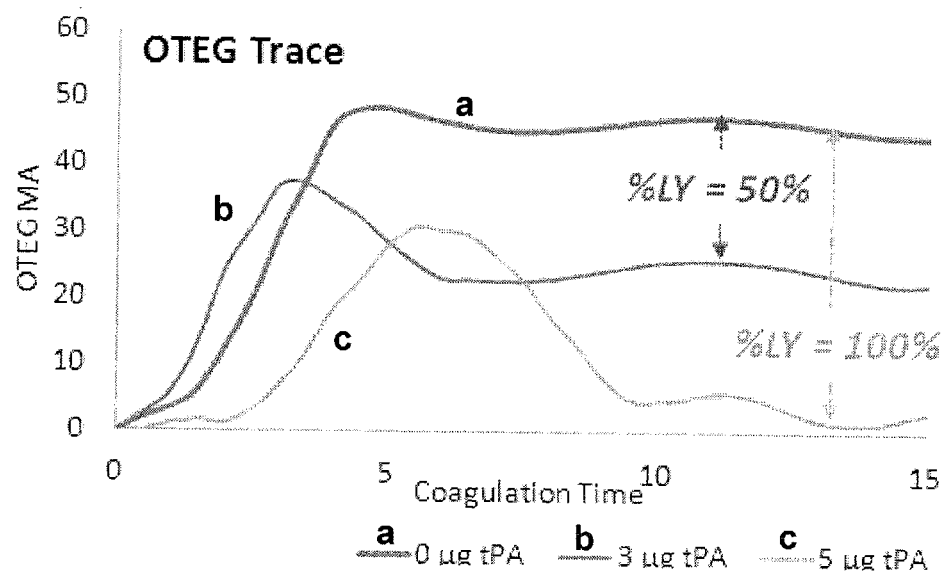
FIGS. 10A, 10B show plots demonstrating the capability to quantify fibrinolysis equivalent to TEG. Normal human blood samples, mixed with kaolin (to activate clotting), are spiked with varying doses of tissue plasminogen activator (tPA) to activate fibrinolysis. The detected dose-dependent changes in % LY values are identical to TEG.
Figure 10B:
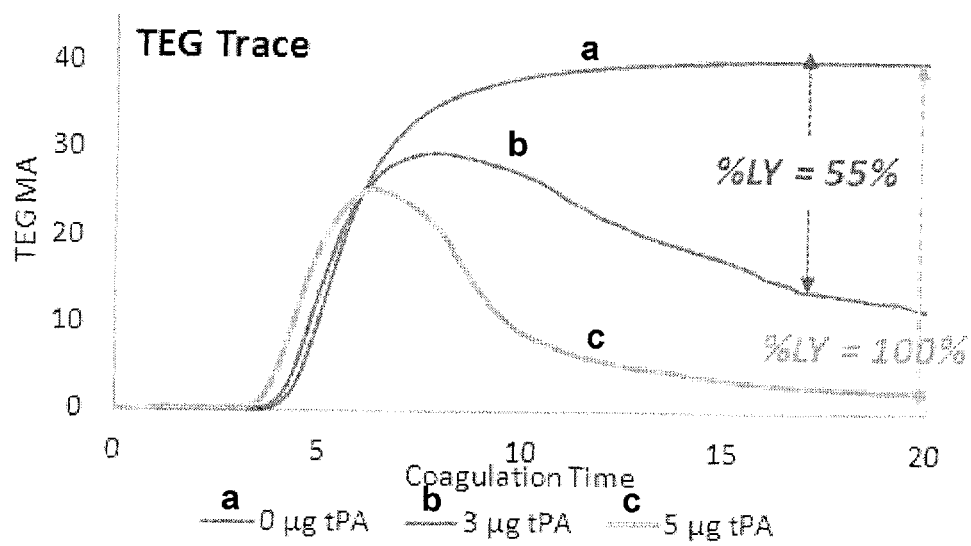

Preliminary studies have established the high accuracy of the bench-top implementation of the OTEG instrument in measuring dose-dependent changes in blood dilution equivalent to TEG (FIGS. 9A, 9B, 9C). Also was established that the OTEG device is capable of measuring fibrinolysis and can measure dose-dependent influence on tissue plasminogen activator (tPA) on % LY values (as shown in FIGS. 10A, 10B, 10C). The protocols selected here similarly permit one to isolate the dose-dependent influence of clotting factors, platelet count, anticoagulant agents and tissue plasminogen on measurements of R, K, $\alpha°$, MA and % LY performed with the use of the embodiment of the hand-held OTEG device and disposable blood cartridges of FIGS. 3 and 4.

Dilutional coagulopathy is generated by serially diluting whole blood (30-60%) with phosphate buffer saline (PBS) solution to vary MA (FIGS. 9A, 9B, 9C). Diluted blood is treated with low to high doses of fibrinogen concentrate (80-160 μL) which also varies MA. Undiluted blood is treated with unfractionated heparin to reach a maximum concentration of 1 U/ml to vary PT, R and K times. To induce fibrinolysis, blood is spiked with varying concentrations of tissue plasminogen activator (tPA) to alter % LY (FIGS. 10A, 10B). Thrombocytopenia or low platelet count is achieved by blood centrifugation, and substitution of platelet-rich with platelet-poor plasma at varying doses, followed by subsequent reconstitution. These samples are then tested using ADP-induced platelet activation (PLT channel) to measure platelet aggregation (as discussed below).

Statistical analysis of the acquired data may include linear regression analysis to evaluate the correlation between OTEG parameters and dose of coagulation variable (dilution, fibrinogen, platelet, heparin and tPA levels). Next, to evaluate OTEG measurement sensitivity, multivariate analysis of variance (MANOVA) tests can be performed to compare groups. If the overall MANOVA test is positive, paired t-tests can be performed to evaluate changes between groups (coagulation variable) and within groups (dosage) from whole blood controls. In one case, a p-value of <0.05 is considered statistically significant. Based on the preliminary studies using serial PBS dilutions of human blood (FIGS. 9A, 9B, 9C) to measure variance in OTEG parameters, it is expected that a sample size oft 5 samples per group is sufficient to allow a difference of 10% in R, MA, % LY, platelet aggregate size, $R_{PLT}$, to be detected between groups with a power of 90% and a significance level of p<0.05.

(III) Platelet Aggregation Analysis:

Platelet aggregation plays a key role in clot initiation and supports many down-stream reactions in the coagulation cascade. The current standard for platelet assessment is light transmission aggregometry (LTA) which evaluates platelet aggregation by measuring changes in turbidity of platelet rich plasma caused by addition of the platelet agonist Adenosine diphosphate (ADP). An LTA-based PoC device is available for clinical use to evaluate platelet aggregation, but it is incapable of assessing other coagulation parameters enabled by the presently disclosed OTEG device (Table 1).

Figure 12A:
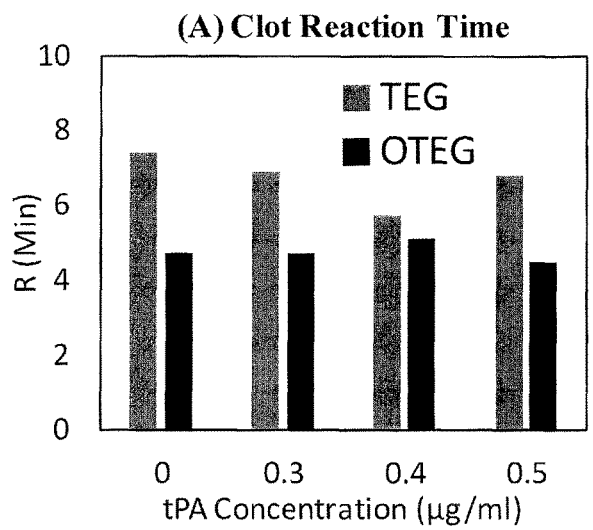
FIGS. 12A, 12B, 12C, 12D, and 12E illustrate the effect of tPA on blood coagulation parameters as measured with an embodiment of the device of the invention in comparison with the results obtained with TEG.
Figure 12B:
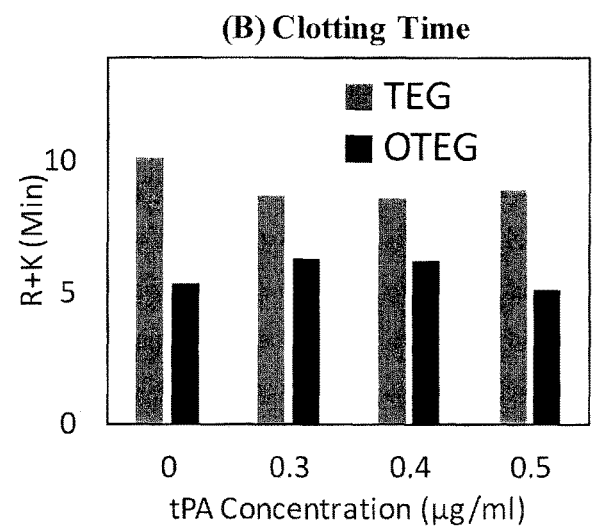
Figure 12C:
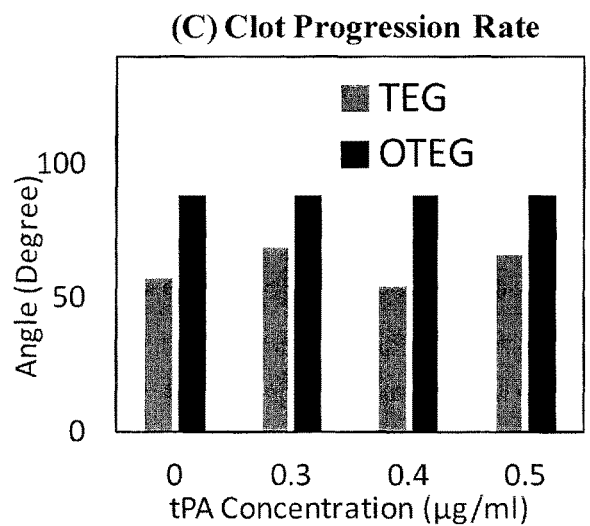
Figure 12D:
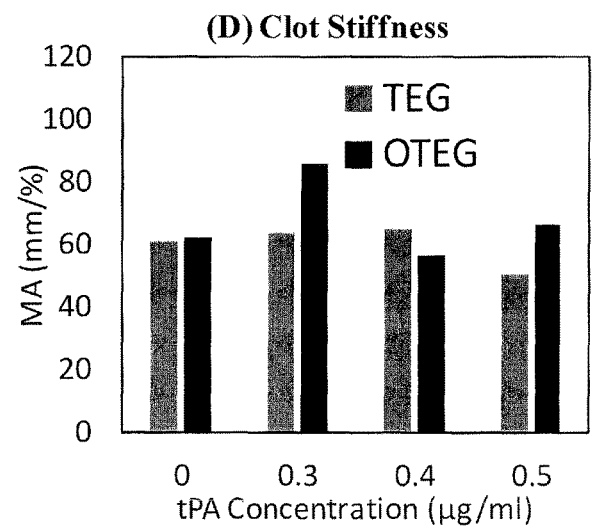

To enable platelet function assessment (PLT channel) via the embodiment of the OTEG device of the present invention, a new strategy was implemented to quantify platelet aggregation in whole blood. To this end, whole blood is mixed with ADP solution and calcium citrate, and time-varying speckle patterns are captured (box 1 of FIG. 5). During the data acquisition, ADP selectively triggers conformational changes in platelets and induces platelet aggregation with minimal influence on RBCs. Thus, an increase in the average scattering particle radius can be predominantly attributed to platelet aggregation. Since the blood is citrated (Ca++ ions are absent), the fibrin cascade is not initiated and blood viscosity, η, remains largely unchanged at η=4 cP (@ 37° C.). Compared to small isolated platelets (dia~3 μm), ADP-induced activation cause large platelet aggregates to appear that experience a shorter range of diffusive motion and induce slower speckle fluctuations. To estimate the rate and extent of platelet aggregation, speckle frames are processed and MSD values are calculated, as above (FIG. 5; box 3). The MSD is automatically fitted to a simple linear model of MSD=6Dt at early times to estimate the diffusion coefficient, D, of scattering particles. The effective particle radius, a, is then obtained from the Stokes-Einstein relation (SER) (FIG. 5: box 4c), the aggregate growth from the baseline at time t=0 is plotted, and the maximum extent of platelet aggregation (RPLT) is estimated at 10 min to quantify platelet function (FIG. 12B). The α-angle is reported as an estimate of platelet aggregation rate. In addition to ADP, other platelet agonists including, for example, collagen, thromboplastin, and von Willebrand factor can be used. In related embodiment, changes in shear rate and/or flow of blood within the chamber could be used to activate platelet aggregation.

Figure 8A:
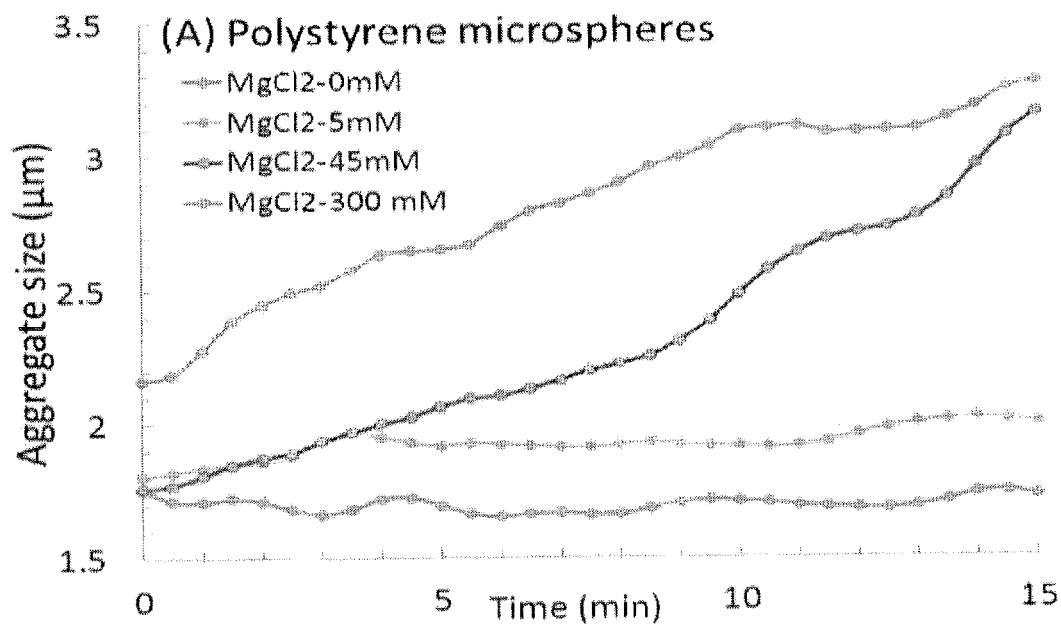
FIGS. 8A, 8B: Preliminary studies to assess platelet aggregation using OTEG methodology.
Figure 8B:
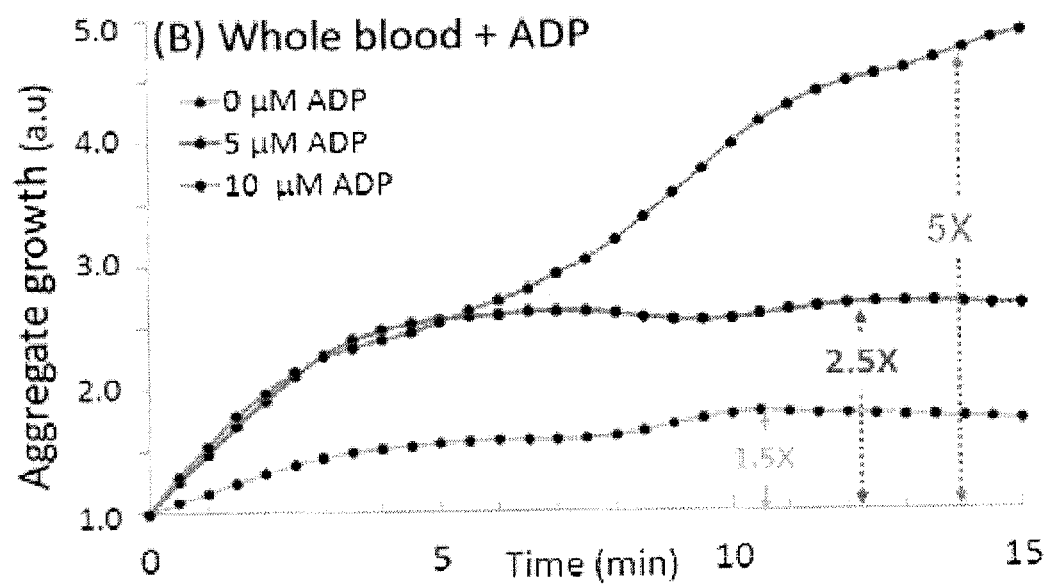

In reference to FIGS. 8A, 8B (and also FIGS. 9A, 9B of WO 2014/100378), this strategy was verified during the preliminary studies, during which $MgCl_2$ solutions were added to the suspensions of polystyrene beads (1.5 μm radius) to initiate clumping. FIG. 8A confirms that OTEG can accurately measure changes in aggregate size induced by tuning MgCl2 concentration. We further verified the capability to detect platelet aggregation in ADP-activated blood and monitored the change of effective aggregate radius. FIG. 8B displays the growth of aggregate radius for ADP concentrations of 0, 5 and 10 μM. Clearly, the effective aggregate radius increase with ADP concentration and can be detected with OTEG with high sensitivity. The results were verified via LTA conducted in the same samples, and by other reports that confirm ADP concentration governs the extent of platelet aggregation (PA).

Empirical Results.

Figure 11A:
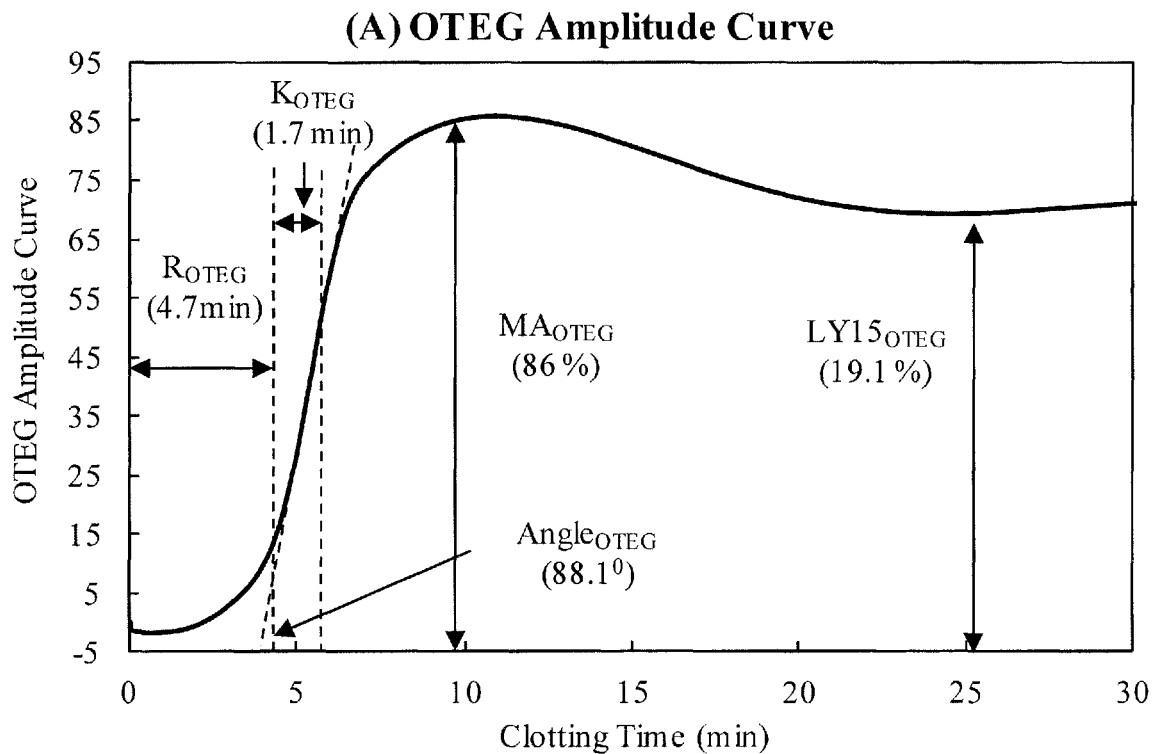
FIGS. 11A, 11B provides comparison of the results of measurements performed on a blood sample with a device configured according to an embodiment of the invention and those carried out with TEG.
Figure 11B:
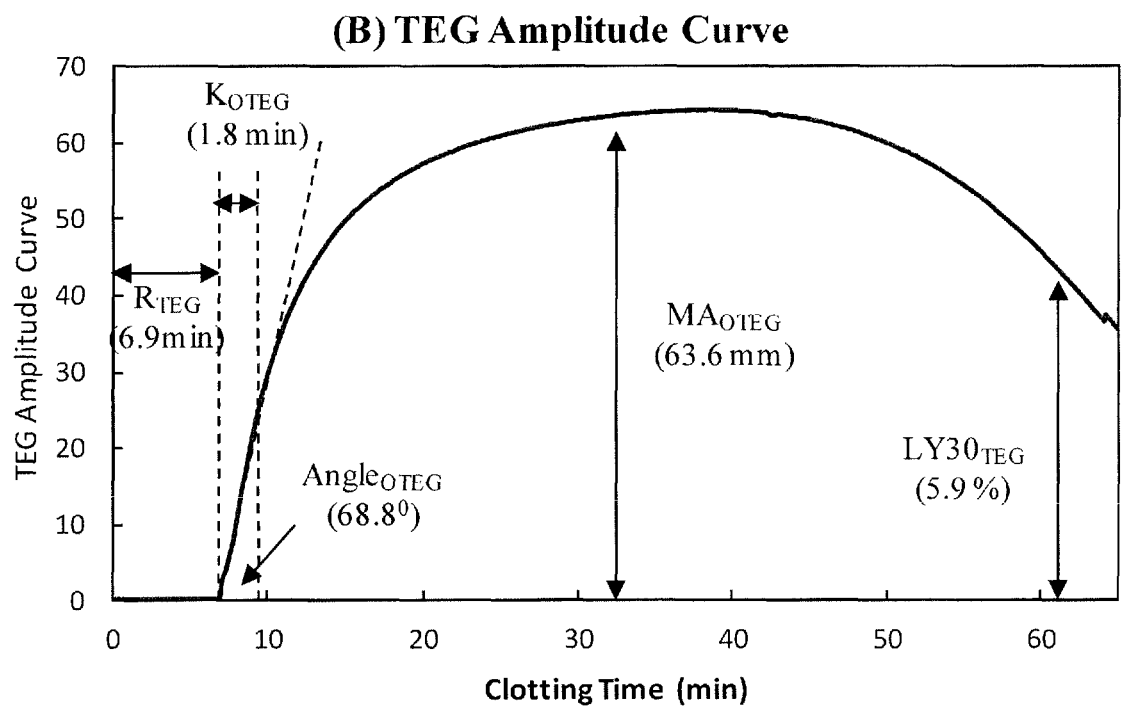

FIGS. 11A, 11B re plots illustrating the comparison of amplitude curves measured with an embodiment of the OTEG device (FIG. 11A) and TEG 5000 (FIG. 11B) for human blood sample. The similarities among the OTEG and TEG amplitude curves can be observed. Advantageously in comparison with the TEG approach, however, the OTEG device possesses better sensitivity to small changes in viscoelasticity as a result of which the detection of such changes takes about half a time as compared to TEG. From the OTEG amplitude curve of FIG. 11A, coagulation parameters, clot reaction time (R), clot progression time (K), maximum clot strength (MA), and fibrinolysis (LY15) are derived. It can be observed that with shorter clotting time (R+K), OTEG attains maximum amplitude in less than half of the time taken by TEG (~10 min in OTEG versus >20 min in TEG). In addition, fibrinolysis can be detected with OTEG within 15 minutes after clot attains maximum stiffness, which enables OTEG to provide information about fibrinolytic activity in a patient in less than 30 minutes. In stark contradistinction, the conventional TEG approach requires an hour to acquire similar information.

Figure 12E:
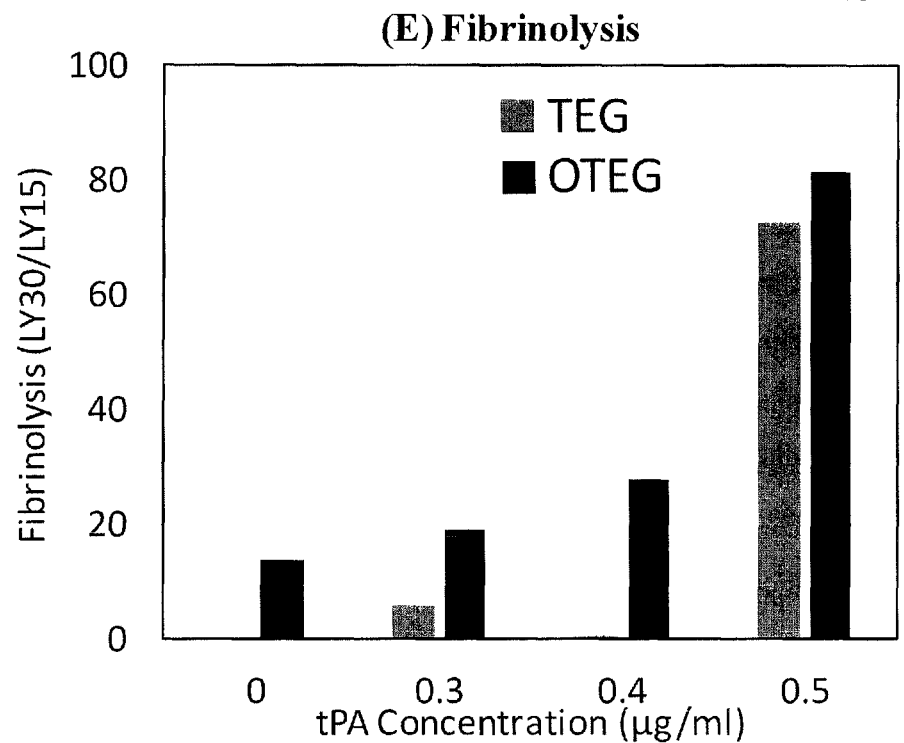

FIGS. 12, 12B, 12C, 12D, and 12E illustrate the effect of tissue plasminogen activator (tPA) on blood coagulation parameters (Clot Reaction Time, Clotting Time, Clot Progression Rate, Clot Stiffness, and Fibrinolysis) measured with OTEG according to an embodiment of the invention and TEG. Here, blood sample from a normal patient was spiked with 0-0.5 μg/ml of tPA to induce varied level of fibrinolytic activity. In FIGS. 12A through 12E, a very similar trend in both OTEG- and TEG-based coagulation-parameter measurements can be observed. However, as shown in FIG. 12E, it can be observed that LY15 measured with OTEG shows better response of tPA induced fibrinolysis in the blood sample in comparison to the same measurement conducted with LY30 in TEG 5000.

Figure 13:
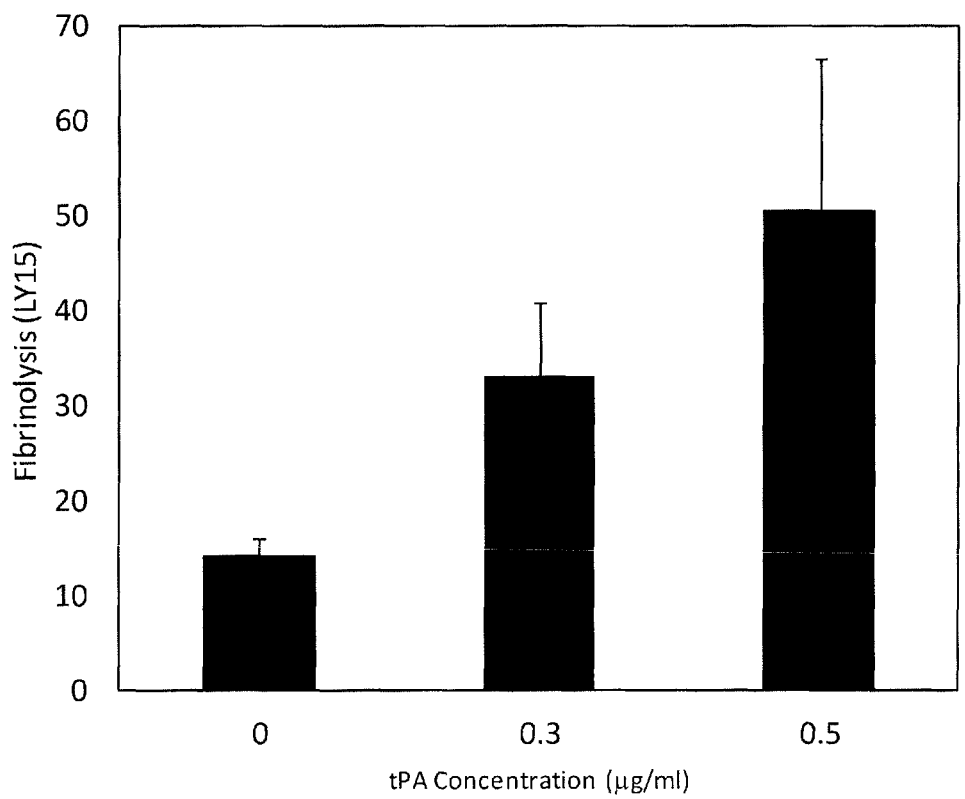
FIG. 13 shows reproducibility of the fibrinolysis measurement in blood samples.

FIG. 13 illustrates reproducibility in OTEG-based fibrinolysis measurement of the parameter LY15 in human blood samples spiked with 0-0.5 μg/ml of tPA. The concentration of tPA from 0 to 0.5 μg/ml increases the fibrinolysis from 14% to 51%, which can be successfully detected with an embodiment of the invention. The error bars represent the standard deviation in the LY15 values obtained from three repeated measurements.

Figure 14:
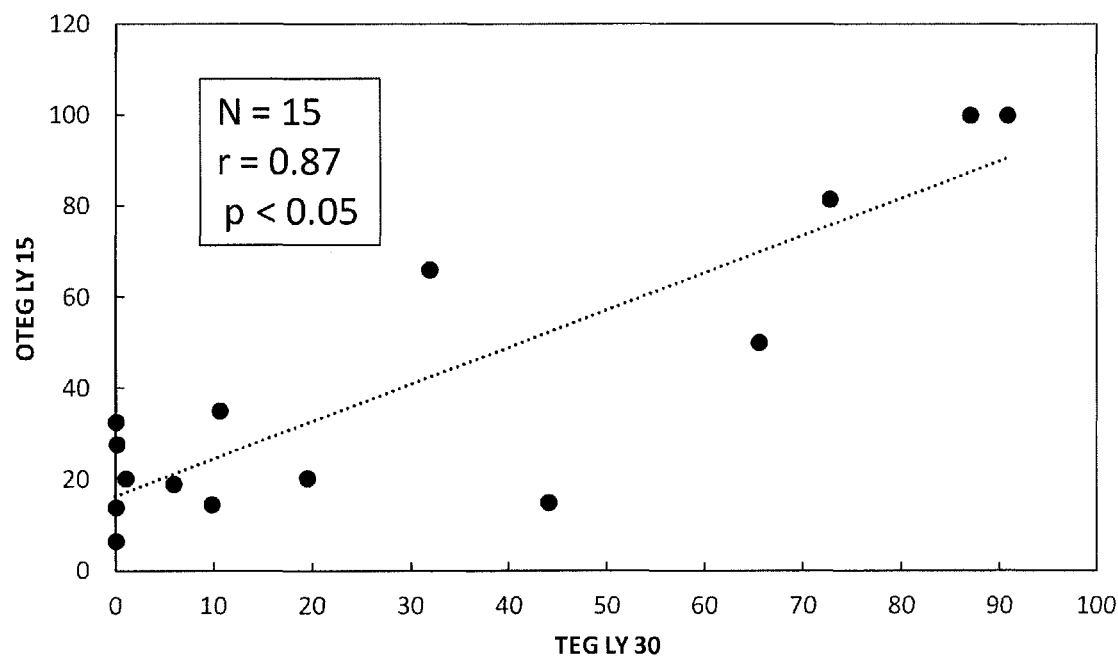
FIG. 14 illustrates comparison of the results of the measurement of fibrinolysis performed with the use of an embodiment of device of the invention and those obtained with TEG.

FIG. 14 is a plot illustrating the comparison of OTEG-based fibrinolysis measurement of LY15 with a corresponding TEG-based measurement of LY30 in a preliminary study (N=15). A strong correlation (r=0.87, p<0.05) in fibrinolytic activity measurements carried out with OTEG and TEG demonstrate the validity of fibrinolysis measurement with an embodiment of the invention.

Figure 15A:
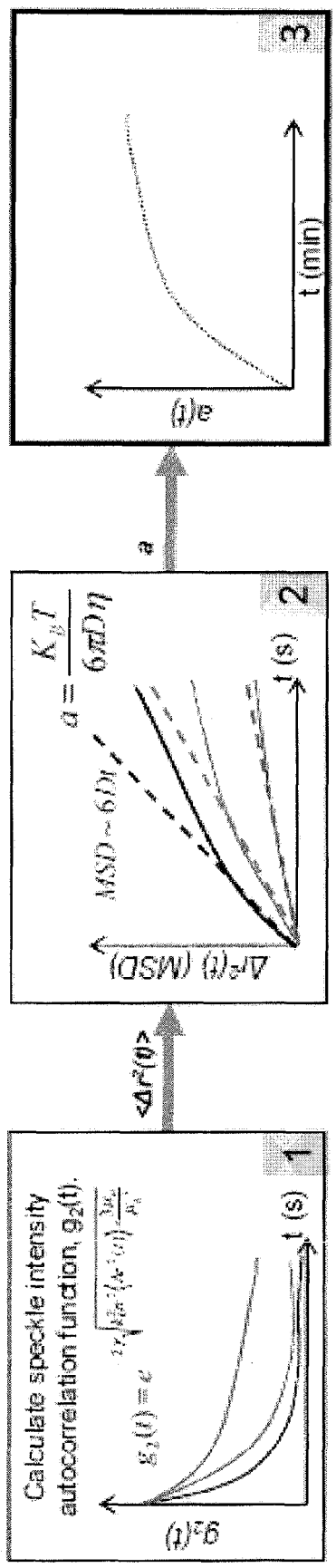
FIG. 15A is a flow-chart of an algorithm for determining the platelet aggregate size from speckle fluctuations in the whole blood.

FIG. 15A is a block-scheme representing an embodiment of the processing algorithm according to the invention for calculating the platelet aggregate size from speckle fluctuations in the whole blood. Citrated whole blood specimen is transferred into an OTEG cartridge, customized for platelet function assessment and preloaded with 40 μl Adenosine 5'-diphosphate solution (Sigma-Aldrich) (i.e. 10 μM final concentration of ADP in the whole blood specimen). The cartridge is inserted in the OTEG device and speckle acquisition begins immediately. During the data acquisition, ADP triggers conformational changes followed by aggregation, which increase the average scattering particle radius. Since $Ca^{++}$ ions are absent, coagulation cascade is not initiated and the blood appears as a primarily viscous liquid with the viscosity of η=4 centipoises (@ 37° C.), particularly at small length scales probed by platelets. As compared to small isolated platelets, large aggregates experience a shorter range of diffusive motion and induce slower speckle fluctuations. To estimate the rate of platelet aggregation, speckle frames are processed and speckle intensity autocorrelation functions are calculated. Since blood is an optically dense material, the mean square displacements (MSD) values of aggregates can be extracted from the $g_2(t)$ curves, using the DWS formalism, as shown in FIG. 15A, box 2. Fitting the MSD to a linear model of MSD=6Dt at early times provides the diffusion coefficient, D, of scattering particles. The effective scattering radius is then obtained from the Stokes-Einstein relation as: $a=K_bT/(6\pi D\eta)$, where $K_b$ is the Boltzman constant and T is the temperature (degrees Kelvin).

Figure 15B:
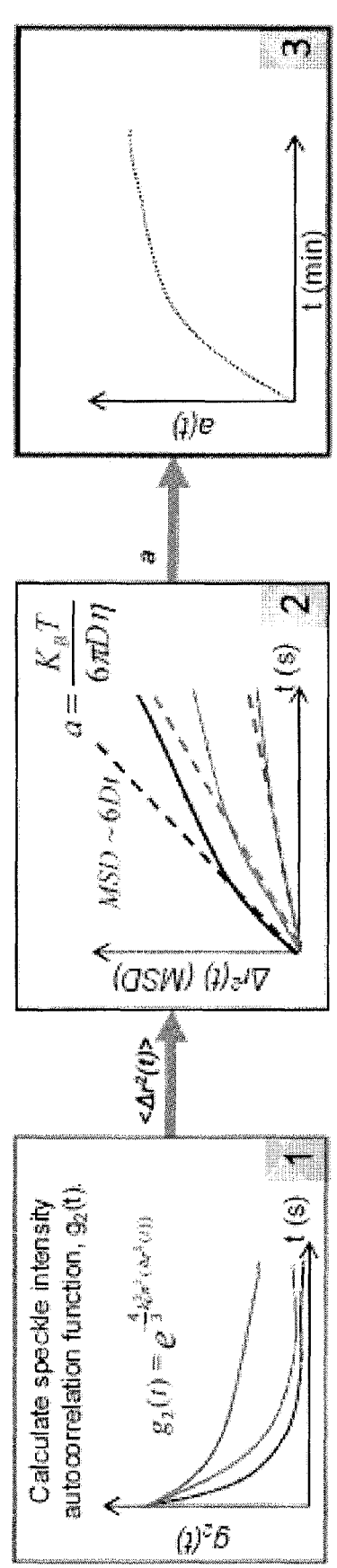
FIG. 15B is a flow-chart of an algorithm for determining the platelet aggregate size from speckle fluctuations in plasma.

FIG. 15B is a block-scheme representing an embodiment of the processing algorithm according to the invention for calculating the platelet aggregate size from speckle fluctuations in the plasma. Platelet rich plasma specimen is transferred into an OTEG cartridge, customized for platelet function assessment and preloaded with 20 μl Adenosine 5'-diphosphate solution (Sigma-Aldrich) (i.e. 5 μM final concentration of ADP in the whole blood specimen). The cartridge is inserted in the OTEG device and speckle acquisition begins immediately. During acquisition, ADP triggers conformational changes followed by aggregation, which increase the average scattering particle radius. Since $Ca^{++}$ ions are absent, coagulation cascade is not initiated and the plasma appears as a primarily viscous liquid with the viscosity of η=3 centipoises (@ 37° C.), particularly at small length scales probed by platelets. Compared to small isolated platelets, large aggregates experience a shorter range of diffusive motion and induce slower speckle fluctuations. To estimate the rate of platelet aggregation, speckle frames are processed and speckle intensity autocorrelation functions are calculated. Since plasma is an optically dilute material, the mean square displacements (MSD) values of platelet aggregates can be extracted from the $g_2(t)$ curves, using the DLS formalism, as shown in FIG. 7(B), box 2. Fitting the MSD to a linear model of MSD=6Dt at early times provides the diffusion coefficient, D, of scattering particles. The effective scattering radius is then obtained from the Stokes-Einstein relation as: $a=K_bT/(6\pi D\eta)$, where $K_b$ is the Boltzman constant and T is the temperature (degrees Kelvin).

Figure 16:
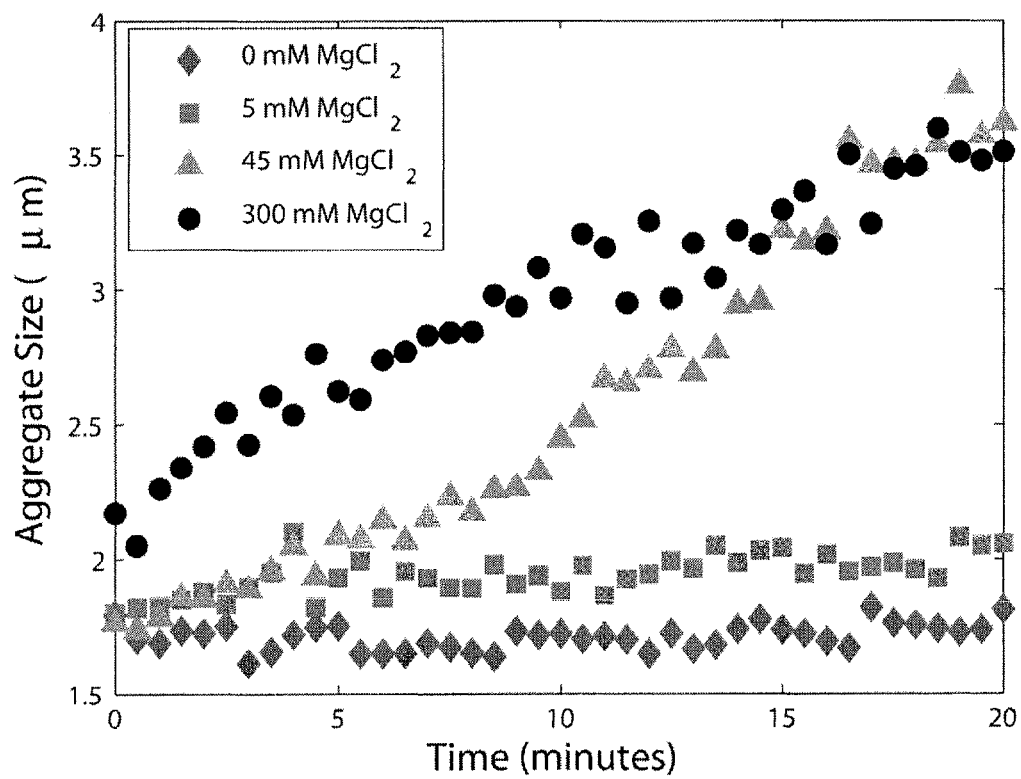
FIG. 16 is a plot representing results of the measurements of aggregate particle size(s) in inorganic materials, carried out with an embodiment of the device according to the invention. The speckle data were processed according to the algorithm of FIG. 17B.

Also practically validated was the capability of the OTEG device to accurately measure aggregate size of particles in inorganic materials. Inorganic salts, such as $MgCl_2$, may be used to trigger the aggregation and clumping of polystyrene bead by changing their surface chemistry. Here, $MgCl_2$ solutions of different molar concentrations were added to the suspensions of polystyrene microspheres (1.5 μm radii, Polysciences, Inc) to initiate particle clumping. The poly-bead plus salt solutions were loaded in OTEG imaging chamber and speckle images were obtained at a high frame rate, such as for instance 750 fps. The speckle images were processed according to the process represented by the flowchart of FIG. 15B, and poly-bead aggregate sizes were calculated as a function of time, past the addition of salt. FIG. 16 displays the trace lines of aggregate vs. time for different salt concentrations and demonstrates that OTEG operation successfully follows and detects particle enlargements at all rates, reflecting the proportionality between the aggregation rate and the salt concentration.

Next, the capability of an embodiment of the OTEG-device for detecting platelet aggregation and monitoring the change of effective aggregate radius was verified with measurements of Adenosine 5'-diphosphate-activated whole blood and plasma.

Figure 17A:
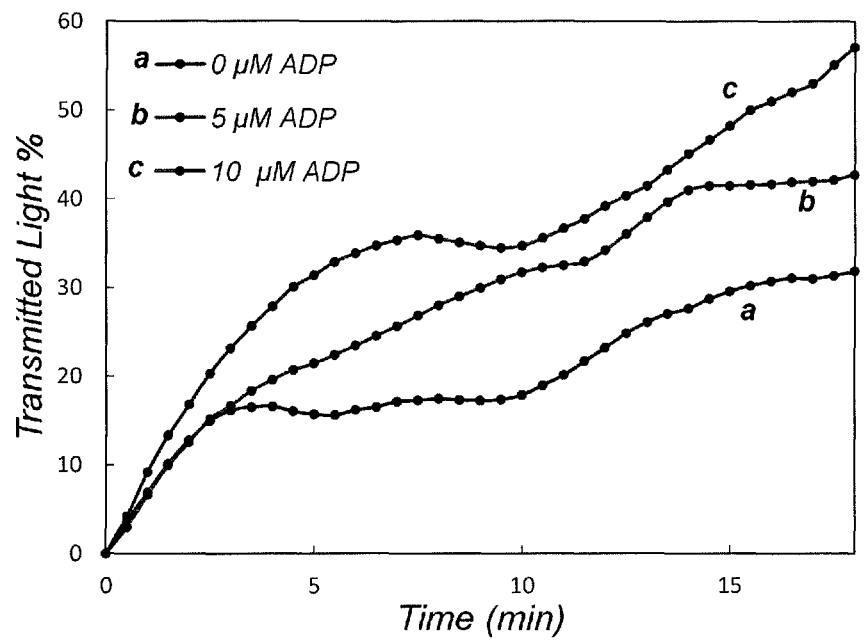
FIG. 17A is a plot representing rate of platelet aggregation in a whole-blood sample measured with an embodiment of the invention in transmittance through the sample.

To this end, FIG. 17A demonstrates the ability of the OTEG embodiment to detect the platelet aggregation rate in whole blood based on the net light transmittance through the specimen. Citrated whole blood specimen was spiked with various concentrations of ADP and transferred into an OTEG cartridge. The cartridge was placed in the OTEG device and speckle images were acquired at both transmission and back-scattering geometry. By incrementing the ADP concentration, platelets formed larger aggregates in a shorter span of time. As a result, the relative turbidity of whole blood rapidly decreased and more light was transmitted through the specimen.

Figure 17B:
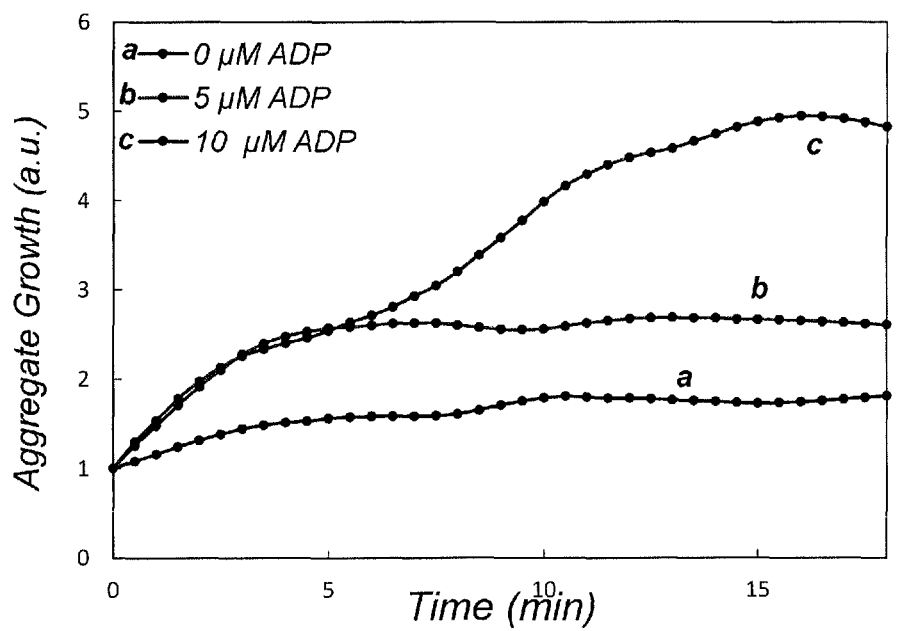
FIG. 17B is a plot representing aggregate size of platelets (from the whole blood sample) determined, based on the measurements carried out with an embodiment of the invention, via an algorithm of FIG. 15A.

FIG. 17B demonstrates the ability of the OTEG device to evaluate the platelet aggregate size in whole blood, based on speckle decorrelation rate. Speckle intensity auto-correlation function, $g_2(t)$ was calculated. The aggregate size was extracted from the $g_2(t)$ curves, using the flowchart of FIG. 15A. The graphs in FIG. 17B depict the growth % of aggregate size for ADP concentrations of 0, 5, and 10 μM, in the same whole blood specimens of FIG. 17A. A person of ordinary skill in the art will readily appreciate that both the rate and ultimate aggregate size increase with ADP concentration. Moreover, the total transmitted intensity, evaluated in FIG. 17A, exhibits close correspondence with the aggregate growth trend, depicted in FIG. 17B.

Figure 18A:
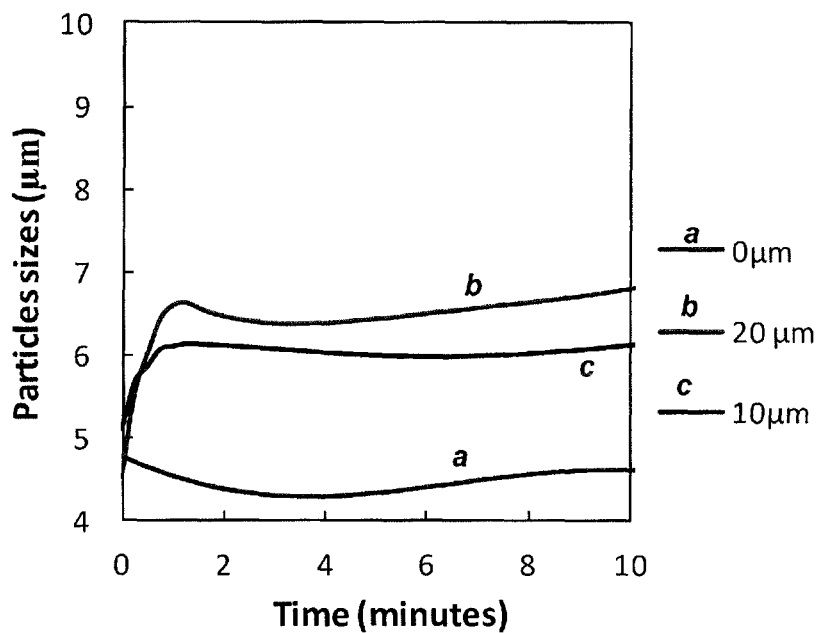
FIGS. 18A, 18B depict profiles of platelet-aggregation in a blood sample with an embodiment of the invention in back-scattering geometry.
Figure 18B:
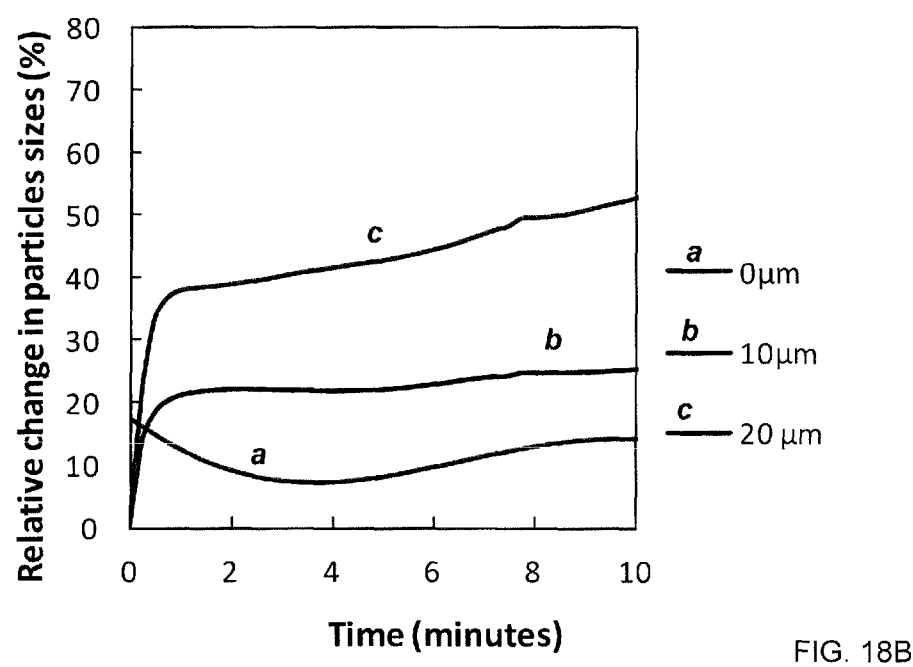

FIGS. 18A, 18B depict platelet aggregation profiles of human blood sample (measured for 10 min with the use of the OTEG device in back scattering geometry) following the treatment with platelet aggregation agonist adenosine diphosphate (ADP) at various concentrations (0 μM-20 μM). FIG. 18A illustrates arbitrary platelet aggregates particles sizes as functions of time, while FIG. 18B represents relative changes in platelet particles sizes (normalized to minima) with time. The information on arbitrary particles sizes was extracted from the fitting to an MSD curve, which was derived from the speckle intensity autocorrelation curve.

Figure 19A:
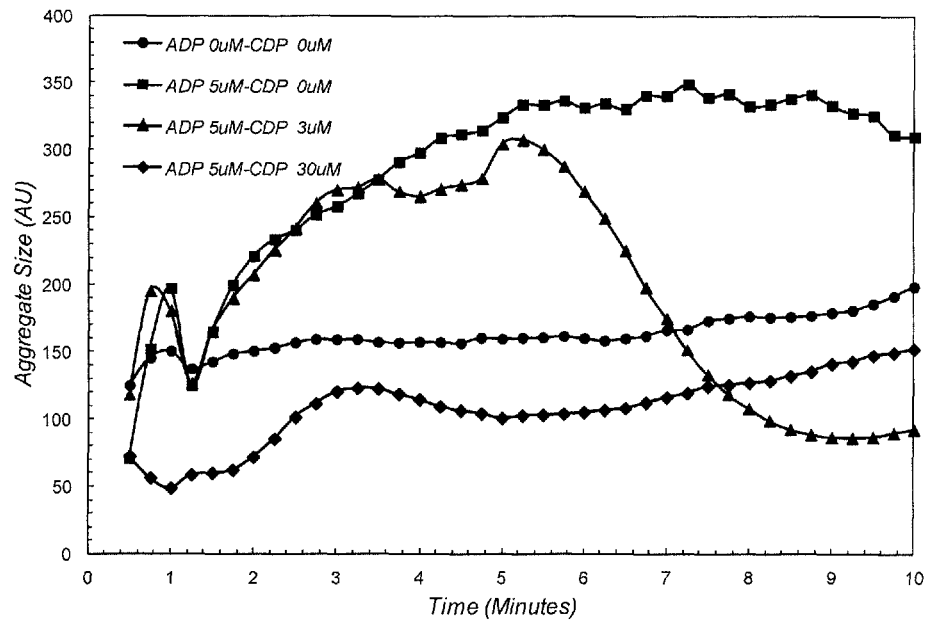
FIGS. 19A, 19B are plots representing empirical results of platelet aggregation in platelet-rich plasma specimen measured with an embodiment of the invention.
Figure 19B:
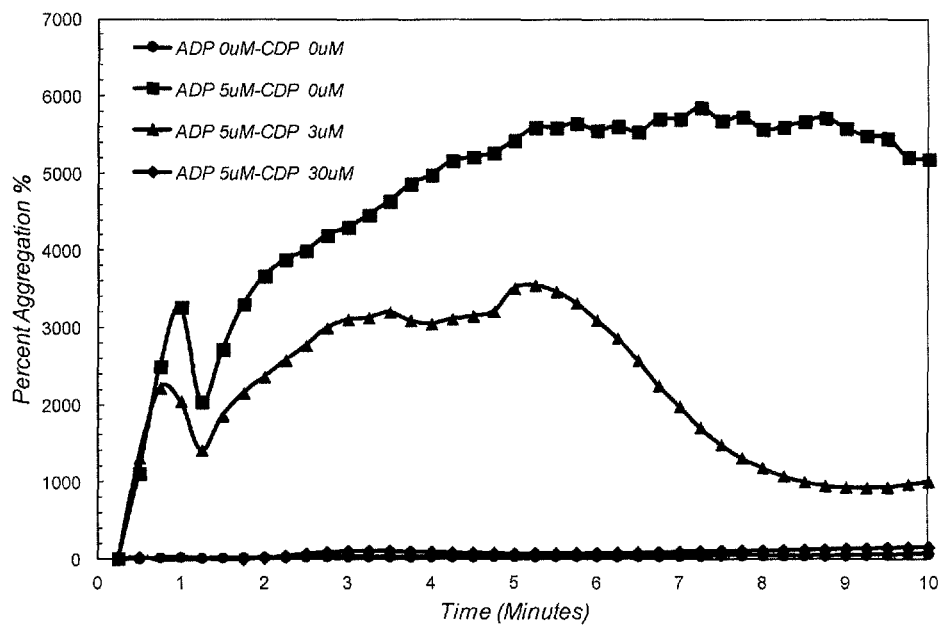

FIG. 19A demonstrates the capability of the OTEG device to detect the platelet aggregation/disaggregation and evaluate the aggregate size in platelet rich plasma specimens, spiked with combinations of platelet agonist ADP, and the antiplatelet agent Clopidogrel. OTEG reports a zero to minimum platelet aggregation in the absence of both ADP and Clopidogrel. By adding ADP with a final concentration of 5 μM to plasma, a rapid and complete platelet aggregation is detected by the OTEG. When both ADP and Clopidogrel with final concentrations of 5 and 3 μM are added to plasma, the OTEG-based measurements reveal a rapid initial aggregation, followed by a rapid disaggregation. Finally, by increasing the Clopidogrel concentration to 30 μM, no aggregation is observed. FIG. 19B provides plots representing percent-aggregation of platelets (plavix: platelet inhibitor) corresponding to the process of FIG. 19A FIGS. 20A, 20B, 20C, 20D, 20E, and 20F demonstrate the capability of OTEG for mapping the platelet aggregation and aggregate size in a small volume of plasma. To obtain these figure, speckle images are captured using expanded beam illumination and magnified acquisition in back-scattering geometry. Next, spatio-temporal speckle processing was used to evaluate speckle intensity autocorrelation function curves, $g_2(t)$, for each and every pixel of the speckle frame series. The $g_2(t)$ curves were the processed according to the flowchart of FIG. 15B to evaluate the size of platelet aggregates, imaged by individual pixels. FIGS. 20A, 20B, 20C present maps of aggregate sizes (in microns) for a plasma specimen with no ADP added. Similarly, FIGS. 20D, 20E, 20F display maps of aggregate sizes (in microns) for a plasma specimen with a final ADP concentration of 10 μM. These figures illustrate the rapid aggregation of platelets within minutes of ADP activation.

For the purposes of the disclosure and claims, the term blood sample refers to any of whole blood and blood constituents (such as platelets and plasma, for example). Overall, to address the problem of efficient and accurate determination of viscoelasticity of a blood sample with the use of light-scattering-based methodology outside of the stationary laboratory, the present invention provides a system for optical analysis of the blood sample, the system including a cartridge. In one implementation cartridge contains: an inlet configured to receive the blood sample; a plurality of analysis chambers in fluid communication with the inlet, each analysis chambers selectively loaded with a corresponding chemical composition to produce a respectively-corresponding speckle pattern in response to light incident onto said analysis chamber from a light source, each speckle pattern being characteristic of at least one blood coagulation metric of a portion of the blood sample contained in the corresponding chamber; and at least one optical port configured to deliver light between an ambient medium surrounding the cartridge and all chambers from the plurality contemporaneously. In such embodiment, at least one blood coagulation metric corresponding to a portion of the blood sample in a first analysis chamber includes clot viscoelesticity and at the least one blood coagulation metric corresponding to a portion of the blood sample in a second analysis chamber includes a platelet aggregation characteristic. The first analysis chamber from the plurality contains a tissue factor, a second analysis chamber from the plurality contains kaolin, and a third analysis chamber from the plurality contains an ADP agonist and anticoagulant. Additionally, the system may include (i) an optical illumination portion configured to deliver light into an analysis chamber from the plurality through the at least one optical port; and (ii) a data acquisition portion including an optical detector unit configured to receive light, that has been delivered into said analysis chamber by the optical illumination portion and that has interacted with a portion of the blood sample contained therein, to acquire optical data representing scattering of said light by multiple light-scattering events within the blood sample. The system is also equipped with a processor operably cooperated with the optical data acquisition portion and programmed a) to determine, based on an autocorrelation function derived from acquired optical data, a time-dependent size of light-scattering particles in the blood sample, which particles cause the multiple light-scattering events; and/or b) to calculate a mean square displacement (MSD) value for the light-scattering particles and a mechanical property of the blood sample from the optical data. Such mechanical property, in one implementation, is a measure of viscoelasticity. Additionally or in the alternative, the processor is programmed to calculate a prothrombin time based on optical data acquired from the first analysis chamber, a viscoelasticity parameter of the blood sample based on optical data acquired from the second analysis chamber, and aggregate size of the light-scattering particles and/or rate of aggregation of light-scattering particles based on optical data acquired from the third analysis chamber. In the system, the optical illumination portion includes a first optical polarizer unit; the optical data acquisition portion includes a second optical polarizer unit, at least one of the first and second optical polarizer units are structured to variably define respectively corresponding first and second polarization states of light transmitted therethrough, the first and second optical polarizer units disposed in optical communication with one another such that light that has passed through the first unit interacts with the plurality of analysis chambers and then passes through the second unit towards the optical detector unit. The cartridge of the system may additionally include a fluid switch through which each of the analysis chambers and the inlet are in fluid communication. Such switch is formed to contain a channel with a step that is step dimensioned to prevent propagation of the blood sample from the inlet to an analysis chamber in absence of an external input applied to the step. The fluid switch further includes a fluid switch pump configured to apply fluidic pressure to said step through a capillary bore located at an interface of said step; a fluid mixing pump fluidly connected with the fluid switch at a point between the inlet and an analysis chamber; and a piston configured to govern an operation of said fluid mixing pump.

Discussed was also a method for optical analysis a blood sample with the use of an optical system. The method includes a step of acquiring (with an optical detector unit of the system through an optical port of a replaceable cartridge of the system), optical data representing time evolution of a speckle pattern defined by light-scattering particles of a portion of the blood sample contained in an analysis chamber of the cartridge. Such analysis chamber is loaded with a chemical composition to produce said speckle pattern that is characteristic of at least one blood coagulation factor of said portion. The method also includes a step of determining a size of the light-scattering particles based on an autocorrelation function derived from acquired optical data; and a step of calculating, with a programmable processor, a value of mean square displacement (MSD) of the light-scattering particles and a mechanical property (such as a viscoelasticity) of the sample from the acquired optical data, said mechanical property being a function of the size of the light-scattering particles. The step of acquiring includes, in one implementation, simultaneously acquiring optical data from each chamber from the plurality of analysis chambers in the cartridge, such that a first analysis chamber from the plurality contains a tissue factor, a second analysis chamber from the plurality contains kaolin, and a third analysis chamber from the plurality contains an ADP agonist and a reagent configured to maintains viscosity of the blood sample unchanged with time. Additional step of such implementation includes calculating prothrombin time based on optical data acquired from the first chamber, a viscoelasticity parameter of the blood sample based on optical data acquired from the second chamber, and aggregate size of the light-scattering particles and rate of aggregation of light-scattering particles based on optical data acquired from the third chamber. In a related embodiment, the step of acquiring includes detecting light in an irradiance distribution, formed at the optical detector unit by light that has interacted with the blood sample, by varying at least one of i) polarization state and ii) wavelength of said light. Alternatively or in addition, the step of determining includes determining a time-dependent size of a light-scattering particle of the blood sample, and the step of calculating includes calculating a viscoelastic parameter of the blood sample.

The method may additionally include i) a step of delivering portions of the blood sample from an inlet of the cartridge to corresponding analysis chambers from the plurality through a fluid switch of the cartridge by applying pressure to a step in a channel of the fluid switch to overcome capillary pressure therein and/or ii) a step of delivering a portion of the blood sample from an inlet of the cartridge to an analysis chamber from the plurality through a spatially twisted channel having a porous inner wall.

Additional information and methodology of determination and calculation of various parameters characterizing cascade of coagulation based on optical data representing light-scattering on particles of a blood sample is described in the international patent application PCT/US2015/014066, the entire disclosure of which is incorporated by reference herein, for all purposes.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

Furthermore, the described features, structures, or characteristics of the invention may be combined in any suitable manner in one or more embodiments. Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Embodiments of the invention have been described as including a programmable processor controlled by instructions stored in a memory. The memory may be random access memory (RAM), read-only memory (ROM), flash memory or any other memory, or combination thereof, suitable for storing control software or other instructions and data. Some of the functions performed by the processor have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the disclosed inventive concepts. The invention should not be viewed as being limited to the disclosed embodiment(s).

The invention claimed is:

1. A system for optical analysis of a blood sample, the system containing a cartridge including:
   i) an inlet configured to receive the blood sample,
   ii) an analysis chamber in fluid communication with said inlet, the analysis chamber loaded with a blood coagulation activator arranged to interact with the blood sample in said chamber, and
   iii) an optical port through which light reaches the analysis chamber;
   an optical detector unit configured to receive light that has been delivered into the analysis chamber through the optical port and that has interacted with the blood sample therein, and to acquire from the light optical data representing scattering of said light by multiple light-scattering events within the portion; and
   a programmable processor operably connected to the optical detector unit and programmed to:
      receive, from the optical detector, optical data representing time evolution of a light scattering from particles of a portion of the blood sample contained in the analysis chamber, the particles comprising components of the blood sample, the optical data including a first image obtained at a first time of light scattered from the interaction between the light and the particles within the portion of the blood sample, the optical data including a second image obtained at a second time of light scattered from the interaction between the light and the particles within the portion of the blood sample;
      determine a value of mean square displacement (MSD) of the particles within the blood sample from the first and the second images; and
      determine a size of the particles including platelet aggregates, based on the MSD value data, wherein the size of the particles is indicative of an extent of platelet aggregation in the blood sample.

2. A system according to claim 1, wherein the components of the blood sample comprises one or more of blood cells, platelets, and platelet aggregates.

3. A system according to claim 1, wherein the programmable processor is further programmed to determine a platelet aggregation characteristic based on the value of MSD of the particles.

4. A system according to claim 3, wherein the programmable processor is further programmed to determine the platelet aggregation characteristic as a function of concentration of the selected blood coagulation activator.

5. A system according to claim 3, wherein the programmable processor is further programmed to determine the platelet aggregation characteristic in a volume of blood plasma.

6. A system according to claim 1, wherein the programmable processor is further programmed to cause the optical detector to simultaneously acquire optical data from each analysis chamber of a plurality of analysis chambers in the cartridge, a first analysis chamber from the plurality containing a tissue factor, a second analysis chamber from the plurality containing kaolin, and a third analysis chamber from the plurality containing a platelet agonist and a reagent configured to substantially maintain viscosity of the blood sample with time.

7. A system according to claim 6, wherein the programmable processor is further programmed to calculate prothrombin time based on optical data acquired from the first chamber, a viscoelasticity parameter of the blood sample based on optical data acquired from the second chamber, and aggregate size of the light-scattering particles and rate of aggregation of light-scattering particles based on optical data acquired from the third chamber.

8. A system according to claim 1, wherein acquiring the optical data includes detecting light from an irradiance distribution, formed at the optical detector unit by light that has interacted with the blood sample, by varying at least one of a i) polarization state and ii) wavelength of the light,
wherein the programmable processor is further programmed to:
determine the size of the particles at least in part by determining a time-dependent size of a light-scattering particle of the blood sample, and determine the value of MSD of the particles at least in part by calculating a viscoelastic parameter of the blood sample.

9. A system according to claim 1, wherein the cartridge further includes a fluid switch configured to deliver portions of the blood sample from an inlet of the cartridge to corresponding analysis chambers from a plurality of analysis chambers by applying pressure to a step in a channel of the fluid switch to overcome capillary pressure therein, wherein the plurality of analysis chambers includes the analysis chamber.

10. A system according to claim 1, wherein the cartridge further includes a spatially twisted channel having a porous inner wall configured to deliver a portion of the blood sample from an inlet of the cartridge to the analysis chamber.

11. A system according to claim 1, wherein the programmable processor is further programmed to determine, from the acquired optical data, fibrinolysis and dose-dependent influence of a tissue plasminogen activator (tPA) on fibrinolysis.

12. A system according to claim 1, wherein the programmable processor is further programmed to derive measures of reaction time, clot formation time, rate of clot formation, maximum clot strength, and fibrinolysis from an amplitude curve obtained, for the blood sample in the cartridge, from the optical data.

13. A system according to claim 1, wherein the programmable processor is further programmed to:
determine an autocorrelation function using the first image and the second image; and
determine the value of MSD of the particles using the autocorrelation function.

14. A method for optical analysis of a blood sample with the use of an optical system, the method comprising:
acquiring, with an optical detector unit of the system through an optical port of a cartridge, optical data representing time evolution of a light scattering from particles of a portion of the blood sample contained in an analysis chamber of the cartridge, the particles comprising components of the blood sample, the analysis chamber loaded with a selected blood coagulation activator, the optical data including a first image obtained at a first time of light scattered from the interaction between the light and the particles within the portion of the blood sample, the optical data including a second image obtained at a second time of light scattered from the interaction between the light and the particles within the portion of the blood sample;
determining a value of mean square displacement (MSD) of the particles within the blood sample from the first and the second images; and
determining a size of the particles based on the MSD value, wherein the size of the particles is indicative of an extent of platelet aggregation in the blood sample.

15. A method according to claim 14, wherein acquiring the optical data includes simultaneously acquiring optical data from each analysis chamber of a plurality of analysis chambers in the cartridge, a first analysis chamber from the plurality containing a tissue factor, a second analysis chamber from the plurality containing kaolin, and a third analysis chamber from the plurality containing a platelet agonist and a reagent configured to substantially maintain viscosity of the blood sample with time.

16. A method according to claim 15, further comprising calculating prothrombin time based on optical data acquired from the first chamber, a viscoelasticity parameter of the blood sample based on optical data acquired from the second chamber, and aggregate size of the light-scattering particles and rate of aggregation of light-scattering particles based on optical data acquired from the third chamber.

17. A method according to claim 14, wherein
acquiring the optical data includes detecting light from an irradiance distribution, formed at the optical detector unit by light that has interacted with the blood sample, by varying at least one of a i) polarization state and ii) wavelength of the light,
determining the size of the particles includes determining a time-dependent size of a light-scattering particle of the blood sample, and
determining the value of MSD of the particles includes calculating a viscoelastic parameter of the blood sample.

18. A method according to claim 14, further comprising delivering portions of the blood sample from an inlet of the cartridge to corresponding analysis chambers from a plurality of analysis chambers through a fluid switch of the cartridge by applying pressure to a step in a channel of the fluid switch to overcome capillary pressure therein, wherein the plurality of analysis chambers includes the analysis chamber.

19. A method according to claim 14, further comprising delivering a portion of the blood sample from an inlet of the cartridge to the analysis chamber through a spatially twisted channel having a porous inner wall.

20. A method according to claim 14, further comprising determining, from the acquired optical data, fibrinolysis and dose-dependent influence of a tissue plasminogen activator (tPA) on fibrinolysis.

21. A method according to claim 14, further comprising deriving measures of reaction time, clot formation time, rate of clot formation, maximum clot strength, and fibrinolysis from an amplitude curve obtained, for the blood sample in the cartridge, from the optical data.

22. A method according to claim 14, further comprising:
determining an autocorrelation function using the first image and the second image; and
determining the value of MSD of the particles using the autocorrelation function.

23. A method according to claim 14, wherein the components of the blood sample comprises one or more of blood cells, platelets, and platelet aggregates.

24. A method according to claim 23, further comprising determining a platelet aggregation characteristic based on the value of MSD of the particles.

25. A method according to claim 24, wherein determining the platelet aggregation characteristic includes determining the platelet aggregation characteristic as a function of concentration of the selected blood coagulation activator.

26. A method according to claim 24, wherein determining the platelet aggregation characteristic includes determining the platelet aggregation characteristic in a volume of blood plasma.

* * * * *

UNITED STATES PATENT AND TRADEMARK OFFICE
CERTIFICATE OF CORRECTION

PATENT NO. : 10,725,018 B2
APPLICATION NO. : 15/319093
DATED : July 28, 2020
INVENTOR(S) : Seemantini K. Nadkarni et al.

Page 1 of 1

It is certified that error appears in the above-identified patent and that said Letters Patent is hereby corrected as shown below:

In the Specification

Column 13, Line 27, "blond" should be --blood--.

Column 16, Line 34, "oft 5" should be --of 15--.

Signed and Sealed this
Eighth Day of September, 2020

Andrei Iancu
*Director of the United States Patent and Trademark Office*